(12) United States Patent
Gerdes et al.

(10) Patent No.: US 7,887,784 B2
(45) Date of Patent: Feb. 15, 2011

(54) 1-[(2'-SUBSTITUTED)-PIPERAZIN-1'-YL]-ISOQUINOLINES AS NOREPINEPHRINE TRANSPORTER INHIBITOR THERAPEUTICS AND POSITRON EMISSION TOMOGRAPHY IMAGING AGENTS

(75) Inventors: John M. Gerdes, Coos Bay, OR (US); David B. Bolstad, Vernon, CT (US); Michael R. Braden, Missoula, MT (US); August W. Barany, Missoula, MT (US)

(73) Assignee: University of Montana, Missoula, MT (US)

( * ) Notice: Subject to any disclaimer, the term of this patent is extended or adjusted under 35 U.S.C. 154(b) by 36 days.

(21) Appl. No.: 12/077,898

(22) Filed: Mar. 21, 2008

(65) Prior Publication Data

US 2008/0267870 A1    Oct. 30, 2008

Related U.S. Application Data

(60) Provisional application No. 60/919,281, filed on Mar. 21, 2007.

(51) Int. Cl.
*A61K 51/04* (2006.01)
*A61K 31/497* (2006.01)
*C07D 401/04* (2006.01)

(52) U.S. Cl. ............... 424/1.81; 514/253.5; 544/363
(58) Field of Classification Search ............... 424/1.81, 424/185; 514/253.05; 544/363
See application file for complete search history.

(56) References Cited

U.S. PATENT DOCUMENTS

| 3,857,944 A | 12/1974 | Simpson |
| 4,324,894 A * | 4/1982 | Benko et al. ............... 544/128 |
| 6,340,759 B1 | 1/2002 | Ueno |
| 2007/0197551 A1 * | 8/2007 | Sato et al. ............... 514/255.05 |

FOREIGN PATENT DOCUMENTS

| CH | 438308 A | 6/1967 |
| EP | 1724267 A | 11/2006 |
| JP | 63227570 A | 9/1988 |
| JP | 2005239578 A | 9/2005 |
| WO | WO 9839301 A | 9/1998 |
| WO | WO 0132626 A | 5/2001 |
| WO | WO 02100822 A | 12/2002 |
| WO | WO 2004080170 A | 9/2004 |
| WO | WO 2006090272 * | 8/2006 |
| WO | WO 2007005935 A | 1/2007 |

OTHER PUBLICATIONS

Gilman H, et al., Rearrangement in the Reaction of Alpha-halogenonaphthalenes with Lithium Diethylamide, J Am Chem Soc, 1945, 2106-08, vol. 67.

Robinson RA, 1-Dialkylaminoalkylminoisoquinolines, J am Chem Soc, 1947, 1932-42, vol. 69.

Cheng YC, et al., Relationship Between the Inhibition Constant (Ki) and Concentration of Inhibitor which Causes 50 Percent Inhibition (IC50) of Enzyme Reaction, Biochem Pharmacol, 1973, 3099-108, vol. 22.

Raisman R, et al., High-affinity [3H]desipramine Binding in the Peripheral and Central Nervous System: a Specific Site Associated with Neuronal Uptake of Noradrenaline, Eur. J Pharmacol, 1982, 345-51, vol. 78.

D'Amato RJ, et al., Selective Labeling of Serotonin Uptake Sites in Rat Brain by [3H]citalopram Contrasted to Labeling of Multiple Sites by [3H]imipramine, J Pharmacol Exp Ther, 1987, 364-71, vol. 242.

Kalaria RN, et al., Adrenergic Receptors in Aging and Alzheimer's Disease: Increased β2-receptors in Prefrontal Cortex and Hippocampus, J Neurochem, 1989, 1772-81, vol. 53.

Tejani-Butt SM, [3H]Nisoxetine: a Radioligand for Qunatitation of Norepinephrine Uptake Sites by Autoradiography or by Homogenate Binding, J Pharmacol Exp Therapeutics, 1992, 426-36, vol. 260.

Tejani-Butt SM, Effect of Age on [3H]nisoxetine Binding to Uptake Sites for Norepinephrine in the Locus Coeruleus of Humans, Brain Res, 1992, 312-15, vol. 583.

(Continued)

*Primary Examiner*—James O Wilson
*Assistant Examiner*—Ebenezer Sackey
(74) *Attorney, Agent, or Firm*—Jean Kyle

(57) ABSTRACT

Racemic mixtures and enantiomerically pure forms of novel 1-[(2'-substituted)-piperazin-1'-yl]-isoquinolines are norepinephrine (NE) transporter (NET) inhibitor compounds. Compounds of the invention are considered therapeutic agents for central nervous system (CNS) diseases and disorders, without limitation, including neurodegeneration, anxiety, depression, attention deficit disorders, drug dependency, and post traumatic stress disorder. Examples of the chemical syntheses of the compounds of the invention are provided. The isoquinoline compounds of the invention competitively bind at NET at nanomolar concentrations. The isoquinoline agents of the invention bind selectively to NET over other competitive transporter targets and receptor binding sites, including those of serotonin and dopamine, amongst others. The chemical syntheses of the invention are suitable for labeling with radionuclide atoms. Radiolabeled forms of the novel 1-[(2'-substituted)-piperazin-1'-yl]-isoquinoline compounds are positron emission tomography and single photon emission tomography imaging tracers. Methods of in vivo imaging with the tracers within various subjects and tissues therein, including regions of the brain, are provided. Imaging methods with the tracers in combination other NET inhibitor agents are provided. The imaging methods within subjects allow quantitative detection of NET, determinations of NET distributions, and measures of tracer interactions at NET in the presence or absence of non-radioactive NET agents. The tracer imaging methods are suitable to locate, diagnose, identify, evaluate, detect or quantitate NET, or abnormalities of NET, or NE abnormalities; that are associated with various CNS diseases and disorders.

13 Claims, 2 Drawing Sheets

OTHER PUBLICATIONS

Naylor A, et al., A Potent New Class of k-receptor Agonists: 4-substituted 1-(arylacetyl)-2-[(dialkylamino)methyl]-piperazines, J Med Chem, 1993, 2075-83, vol. 36.

Tejani-Butt SM, et al., Norepineprhine transporter sites are decreased in the locu coeruleus in Alzheimer's disease, Brain Res, 1993, 147-50, vol. 631.

Hoye TR, et al., MTPA (Mosher) Amides of Cyclic Secondary Amines: Conformational Aspects and a Useful Method for Assignment of Amine Configuration, J Org Chem, 1996, 205, vol. 65.

Klimek V, et al., reduced Levels of Norepinephrine Transporters in the Locus Coeruleus in Major Depression, J Neurosci, 1997, 8451-58, vol. 17.

Ordway GA, Pathophysiology of the Locus Coeruleus in Suicide, Ann NY Acad Sci 1997, 233-52. vol. 836.

Owens MJ, et al., Neurotransmitter Receptor and Rransporter Binding Profile of Antidepressants and Their Metabolites, J Pharmacol Exp Ther, 1997,1305-22, vol. 283.

Rondu F, et al., Design and Synthesis of Imidaoline Derivatives Active on Glucose Homeostasis in a Rat Model of Type II Diabetes. 1. Synthesis and Biological Activities of N-benzylN'-(arlalkyl)-2(4',5'-dihydro-1'HH-imidazol-2'-yl) piperazines, J Med Chem, 1997, 3793-803, vol. 40.

Gerdes JM, et al., Serotonin Transporter Inhibitors: Synthesis and Binding Potency of 2'-methyl- and 3'-methyl-6-nitroquipazine, Bioorg Med Chem Lett, 2000, 2643-46, vol. 10.

Millan MJ, et al., Reciprocal Autoreceptor and Heteroreceptor Control of Serotonergic, Dopaminergic, and Adrenergic Transmission in the Frontal Cortex: a Review, and Relevance to the Actions of Antidepressant Agents, J Pharmacol, 2000, 114-38, vol. 14.

Tai C, et al., Performance Evaluation of the MicroPET P4: a PET System Dedicated to Animal Imaging, Phys Med Biol, 2001, 1845-62, vol. 46.

Bymaster FP, et al., Atomoxetine Increases Extracellular Levels of Norepinephrine and Dopamine in Prefrontal Cortex of Rat: a Potential Mechanism for Efficacy in Attention Deficit/Hyperactivity Disorder, Neuropsychopharmacology, 2002, 699-711, vol. 27.

Cannistraro PA, et al., Neural Circuitry of Anxiety: Evidence from Structural and Functional Neuroimaging Studies, Psychopharmacol Bull, 2003, 8-25, vol. 37.

Leoning AM, et al., AMIDE: a Free Software Tool for Multimodality Medical Image Analysis, Molecular Imaging, 2003, 131-37, vol. 2.

Schou M, et al., Specific In Vivo Binding to the Norepinephrine Transporter Demonstrated with PET Radioligant (S,S)-[11C]MeNER, Nuc Med Biol, 2003, 707-14, vol. 30.

Bedurftig S, et al., Chiral, Nonracemic (piperazin-2-yl)methanol Derivates with sigma-receptor affinity, Bioorg Med Chem, 2004, 3299-3311, vol. 12.

Hajos M, et al., the Selective Norepinephrine Reuptake Inhibitor Antidepressant Reboxetine: Pharmacological and Clinical Profile, CNS Drug Reviews, 2004, 23-44, vol. 10.

Schou M, et al., PET Evaluation of Novel Radiofluorinated Reboxetine Analogs as Norepinepthrine Transporter Probes in the Monkey Brain, Synapse, 2004, 57-67, vol. 53.

Yang Y, et al., Optimization and Performance Evaluation of the MicroPET II Scanner for In Vivo Small-animal Imaging, Phys Med Biol, 2004, 2527-45, vol. 49.

Zhou J, Norepinephrine Transporter Inhibitors and Their Therapeutic Potential, Drugs Future, 2004, 1235-44, vol. 29.

Ding Y-S, et al., PET Imaging of Norepinephrine Transporters, Current Pharmaceutical Design, 2005, 3831-45, vol. 12.

Logan J, et al., Modeling and Analysis of PET Studies with Norepinephrine Transporter Ligands: the Search for a Reference Region, Nuc Medicine and Biology, 2005, 531-42, vol. 32.

Russo EB, et al., Agonist Properties of Cannabidiol at 5-HT1a Receptors, Neurochem Res, 2005, 1037-43, vol. 30.

Stone EA, et al., The Brain Epinephrine-alpha1-adrenoreceptor System in Behavioural Activation and Depression, Current Psychiatr Rev, 2005, 33-43, vol. 1.

Tai YC, et al., Performance Evaluation of the MicroPET Focus: a Third Generation MicroPET Scanner Dedicated to Animal Imaging, J Nuc Med, 2005, 455-63, vol. 46.

Bedurftig S, et al., Synthesis and Receptor Binding Studies of 3-substituted Piperazine Derivatives, Eur J Med Chem, 2006, 387-96, vol. 41.

Bonisch H, et al., The Norepinephrine Transporter in Physiology and Disease, Handbook of Experimental Pharmacology, 2006, 485-525, vol. 175.

Ding Y-S, et al., Comparative Evaluation of Positron Emission Tomography Radiotracers for Imaging the Norepinephrine Tranporter: (S,S) and (R,R) Enantiomers of Reboxetine Analogs ([11C]methylreboxetine, 3-Cl-[11C] methylreboxetine and [18F]fluororeboxetine), (R)-[11C]nisoxetine, [11C]oxaprotiline, and [11C]lortalamine, J Neurochem, 2006, 337-51, vol. 94.

Madela P, et al., The Norepinephrine Transporter and Its Regulation, J Neurochem, 2006, 310-333, vol. 97.

Millan MJ, Multi-target Strategies for Improved Treatment of Depressive States: Conceptual Foundations and Neuronal Substrates, Drug Discovery and Therapeutic Application, Pharmacol and Therapeutics, 2006, 135-370, vol. 110.

Seneca N, et al., Atomoxetine Occupies the Norepinephrine Transporter in a Dose-dependent Fashion: a PET Study in Nonhuman Primate Brain Using (S,S)-[18F]FMeNER-D2, Psychopharmacol, 2006, 119-27, vol. 188.

Smith HR, et al., Distribution of Norepinephrine Transporters in the Non-human Brain, Neurosci, 2006, 703-14, vol. 138.

Vieweg WV, et al., Posttraumatic Stress Disorder: Clinical Features, Pathophysiology, and Treatment, Am J Med, 2006, 383-90, vol. 119.

Logan J, et al., Imaging the Norepinephrine Transporter in Humans with (S,S)-[11C]O-methyl Reboxetine and PET: Problems and Progress, Nuc Med Biol, 2007, 667-79, vol. 34.

Rommelfanger KS, et al., Norepinephrine: the Redheaded Stepchild of Parkinson's Disease, Biochem Pharmacol, 2007, 177-90, vol. 74.

Tamagnan GD, et al., Development of SPECT Imaging Agents for the Norepinephrine Transporters: [123I]INER, Bioorg Med Chem Lett, 2007, 533-37, vol. 17.

* cited by examiner

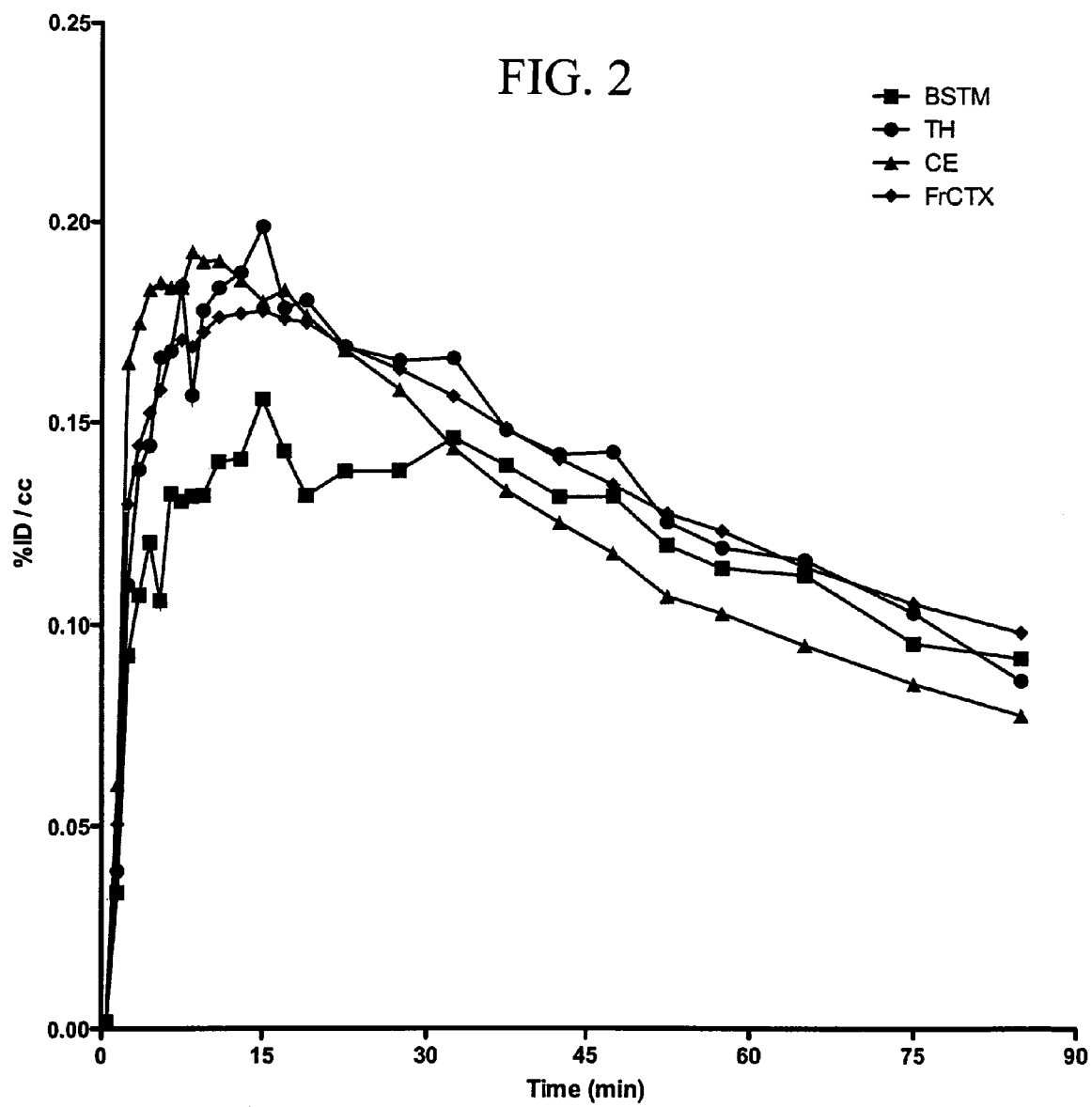

1-[(2'-SUBSTITUTED)-PIPERAZIN-1'-YL]-ISOQUINOLINES AS NOREPINEPHRINE TRANSPORTER INHIBITOR THERAPEUTICS AND POSITRON EMISSION TOMOGRAPHY IMAGING AGENTS

CROSS-REFERENCE TO RELATED APPLICATIONS

This application claims the benefits of U.S. Provisional Application No. 60/919,281 filed Mar. 21, 2007, the disclosure of which is hereby incorporated by reference in its entirety including all figures, tables and drawings.

STATEMENT REGARDING FEDERALLY SPONSORED RESEARCH OR DEVELOPMENT

This invention was made in part with Government support under Grant No. 5 P20 RR015583 awarded by the NIH. The government has certain rights in the invention.

REFERENCE TO SEQUENCE LISTING, A TABLE, OR COMPUTER PROGRAM LISTING COMPACT DISC APPENDIX

Not Applicable

BACKGROUND OF THE INVENTION

The norepinephrine transporter (NET) protein found within peripheral and central nervous system (CNS) tissues is responsible for the clearance of the endogenous neurotransmitter norepinephrine (NE) from the synaptic cleft after neuronal firing. Chemical agents that inhibit NE synaptic clearance (reuptake) by the NET by binding at the NET (inhibitor binding) serve to enhance NE synaptic concentrations. The CNS biomedical literature describes that NET inhibitor drugs and related agents that enhance NE synaptic concentrations are indicated with anti-anxiety, antidepressant, and improved cognitive qualities [Millan 2006]. Additionally, NET interacting inhibitor-based binding drugs and similar ligands, have the ability to alter the perception of pain [Millan 2006] and influence the outcomes of attention deficit disorders, post traumatic stress disorder (PTSD), and related co-morbid psychiatric states through the modulation of NE neurotransmission within the CNS [Rommelfanger 2007, Bonish 2006, Stone 2005, Cannistraro 2003, Millan 2000].

Examples of CNS NET inhibitor binding drugs include desipramine, (S,S)-reboxetine, atomoxetine, and (S)-duloxetine [Mandela 2006, Millan 2006, Hajos 2004, Zhou 2004, Bymaster 2002]. The drugs are thought to promote some of their beneficial effects by modulating NE synaptic concentrations by blocking reuptake of NE at NET. Effective compositions of the drugs include salts; for example, with duloxetine as the hydrochloride (HCl) salt. The drugs are characterized with in vitro pharmacological NET inhibitor competitive binding affinities ($K_i$ value) in the moderate to low nanomomolar concentration range. Many of the established NET inhibitor binding drugs and agents also possess cross binding interactions with other CNS target proteins; defining them with NET non-selective binding profiles. In particular, the other cross binding interactions include the serotonin transporter (SERT) and the dopamine transporter (DAT) [Mandela 2006, Millan 2006] proteins.

Drugs and ligands that are highly selective for and potent at NET are considered as potential CNS therapeutics [Millan 2006, Zhou 2004, Bymaster 2002] for certain NE-based psychiatric disorders and diseased states. Structurally novel NET inhibitor agents devoid of promiscuous CNS binding (e.g., SERT and/or DAT interactions, amongst other sites) are few. Examples of NET potent and selective agents include stereochemical forms of ligand nisoxetine [Tejani-Butt 1992], which when labeled with a radioactive atom such as tritium ($[^3H]$) are capable of the quantitative detection of NET in tissues [Smith 2006, Tejani-Butt 1992 & 1993].

Pharmacologically potent and selective NET inhibitor agents which are appended with select positron emitting radionuclide atoms (e.g., carbon-11, fluorine-18, bromine-76, iodine-122, iodine-124, iodine-131) at select locations on the chemical structures, can serve as quantitative positron emission tomography (PET) imaging tracers for the NET target protein in live brain [Ding 2006 & 2005, Logan 2007 & 2005]. Examples include the NET PET imaging tracers (S,S)-[$^{11}$C]MeNER and (S,S)-[$^{18}$F]FMeNER which have chemical structures possessing two aromatic ring moieties joined by a heteroatom linkage [Ding 2006 & 2005, Seneca 2006, Schou 2004 & 2003]. Examples of NET PET imaging tracers capable of detecting and quantifying NET protein density in a reproducible manner within discrete tissue regions (for example within brain) are limited [Logan 2007 & 2005, Ding 2006, Seneca 2006]. Similarly, NET inhibitor agents appended with other radionuclides (for example, iodine-123) may serve as single photon emission computed tomography (SPECT) imaging agents [Tamagnan 2007].

Structurally novel NET PET and SPECT imaging tracers, that are defined as classes of compounds with demonstrated in vitro NET binding selectivity and potency, are useful for the detection and quantification of NET by in vivo and in vitro methods within the clinic and laboratory [Logan 2007 & 2005, Smith 2006, Tejani-Butt 1992 & 1993]. Since select CNS disorders and diseases are thought to be a result of abnormalities associated with NET or the NE system, then detection and quantification of NET in select tissues provides a method for diagnoses [Logan 2007 & 2005]. The detection of NET and the determination of altered tissue NET density (concentration) in regions of interest (ROIs) by in vivo PET imaging, and related in vitro tracer methods [Smith 2006, Tejani-Butt 1992 & 1993], can be indicative and diagnostic of select CNS diseases, disorders, and abnormalities resultant from NET or NE pathway dysregulations.

For example, with brain tissues the detection and quantification of NET by dynamic tissue imaging methods provides a means for the diagnosis of select neuropathologies [Tejani-Butt 1992 & 1993, Logan 2007 & 2005, Ding 2006 & 2005] and mental health disorders, not limited to neurodegenerative conditions, anxiety, depression, attention deficit disorders, drug dependency, post traumatic stress disorder, among others [Rommelfanger 2007, Ding 2006 & 2005, Vieweg 2006, Klimek 1997, Ordway 1997]. Additionally, with a NET PET tracer NET target protein occupancy of other non-radioactive NET inhibitor drugs and agents [Logan 2007, Seneca 2006] may be assessed. For example, the analysis by quantitative imaging of competitive NET binding between a tracer and non-radioactive drug or agent provides an understanding of in vivo dynamic competitive NET binding and pharmacokinetic performance of agents within tissues (including brain) over time [Logan 2007, Ding 2006, Seneca 2006, Schou 2004 & 2003, Tamagnan 2007].

All patents, patent applications, provisional patent applications and publications referred to or cited herein, are incorporated by reference in their entirety to the extent they are not inconsistent with the teachings of the specification.

BRIEF SUMMARY OF THE INVENTION

The invention encompasses structurally novel 1-[(2'-substituted)-piperazin-1'-yl]-isoquinoline compounds that possess potent and selective binding affinity for the norpeinephrine transporter (NET) protein found in peripheral and central nervous system tissues. The compounds of the invention are with novel chemical structures distinct from other NET inhibitor binding drugs and agents. The compounds of the invention are characterized with pharmacologically potent binding at the NET in brain tissues, amongst others. The compounds possess high selectivity for the NET target protein relative to other competing drug protein binding sites in tissues. The compounds of the invention can be used in the treatment or prophylaxis of diseases and disorders characterized by NET or NE abnormalities; where diseases and disorders, without limitation include anxiety, depression, attention deficit disorder, drug dependency, post traumatic stress disorder, and neurodegenerative disorders co-morbid with abnormalities of NET or NE.

The invention encompasses radioactive tracer forms of the compounds, which have radioactive atoms bonded to carbon atoms of the compound structures. The tracers are used to quantitatively detect NET and NET distributions using in vivo and in vitro imaging methods. The imaging tracers detect and quantify NET densities within live and post-mortem tissues, including brain. The tissue imaging methods encompass positron emission tomography (PET), single photon emission computed tomography (SPECT) and autoradiography. For live tissue imaging, preferably the radiotracers of the invention can be administered to subjects in an amount suitable for in vivo imaging thereof, and to locate, diagnose identify evaluate detect and quantify NET in CNS diseases and disorders, without limitation including anxiety, depression, attention deficit disorder, drug dependency, post traumatic stress disorder, and neurodegenerative disorders co-morbid with abnormalities of NET or NE. The invention provides examples using the tracers with PET imaging methods for the quantitative detection of NET and NET distributions within live brain tissues of various subjects.

The 1-[(2'-substituted)-piperazin-1'-yl]-isoquinoline general structure of the compounds and tracers of the invention is the following.

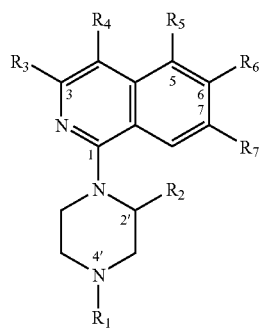

The compounds and radiolabeled tracers of the invention include analogs, salts, compositions, derivatives, pro-drugs and discrete configurational stereochemical constitutions (racemic mixtures or enantiomeric stereochemical forms) thereof. The invention provides examples of methods for syntheses of the compounds. The invention provides examples of methods for radiolabeling for the production of the tracers of the invention.

BRIEF DESCRIPTION OF THE SEVERAL VIEWS OF THE DRAWINGS

FIG. 2 shows the in vivo PET imaging quantitative detection and distribution of the NET within tissues of a primate subject brain, male rhesus monkey, with tracer time-activity pharmacokinetic curves afforded after dose administration of the radiotracer (S)-[$^{18}$F]28; where the Y axis is injected tracer dose per cubic centimeter (% ID/cc) tissue values and the X axis is time in minutes; and as per the figure legend solid line curves and solid symbols are NET detection and distribution values acquired by dosing tracer alone where the curves are defined (figure legend) for brain tissues including BSTM as brain stem (square symbol), TH as thalamus (circle symbol), CE as cerebellum (triangle up symbol), and FrCTX as frontal cortex (diamond symbol).

DETAILED DESCRIPTION OF THE INVENTION

Figure 1:
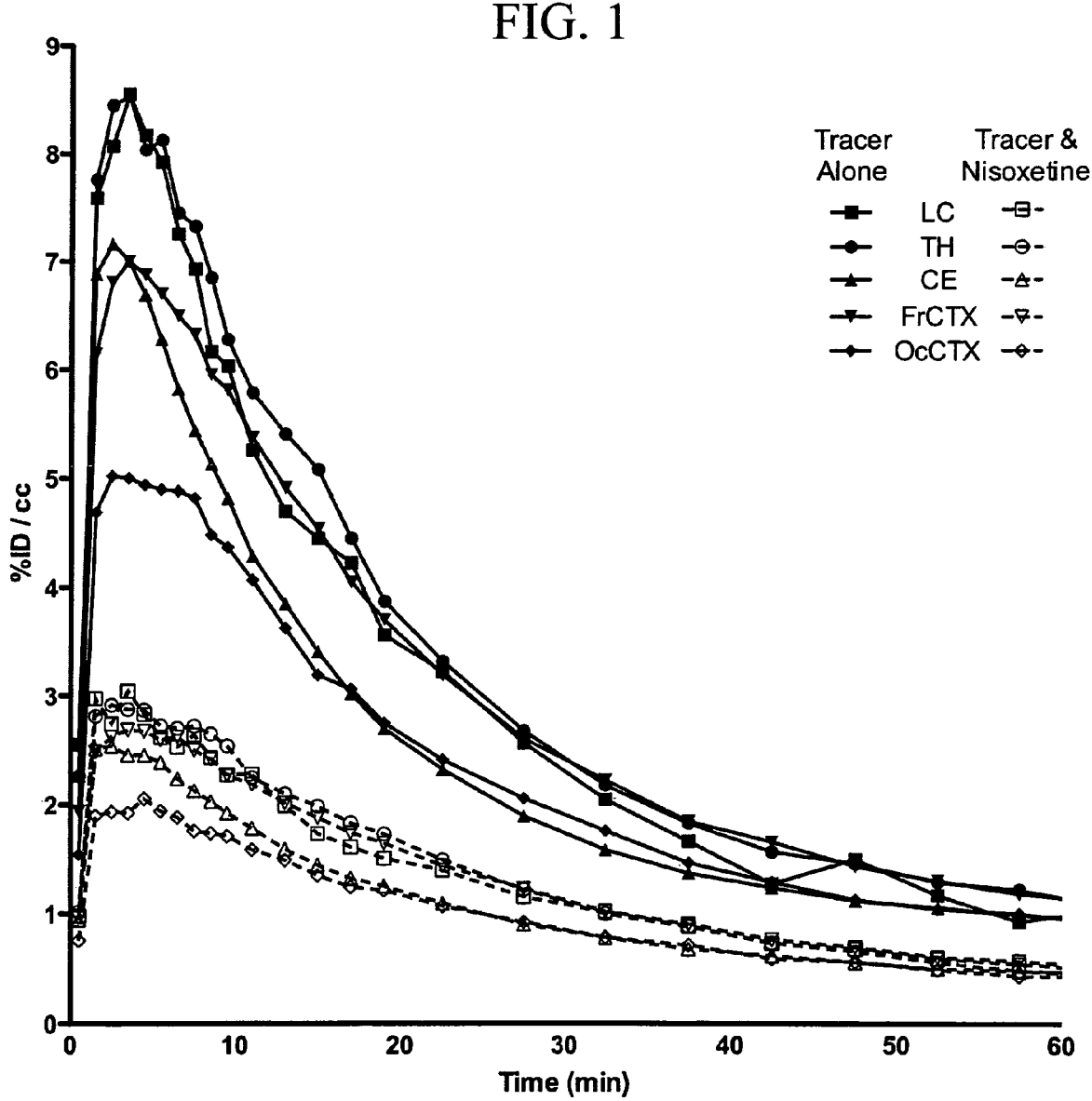
FIG. 1 shows the in vivo PET imaging quantitative detection and distribution of NET within female rat subject brain tissues with tracer time-activity pharmacokinetic tissue curves afforded after dose administration of the radiotracer (±)-[$^{18}$F]28, where the Y axis is injected tracer dose per cubic centimeter (% ID/cc) tissue values and the X axis is time in minutes; and as per the figure legend solid line curves and solid symbols are NET detection and distribution values acquired by dosing tracer alone (unblocked), whereas the dashed line curves and open symbol forms are time-activity tracer profiles that are afforded by dosing the subject with the known NET inhibitor agent (±)-nisoxetine (2.0 mg/Kg dose, blocked); and where the curves are defined (figure legend) for brain tissues including LC as locus ceruleus (square symbol), TH as thalamus (circle symbol), CE as cerebellum (triangle up symbol), FrCTX as frontal cortex (triangle down symbol), and OcCTX as occipital cortex (diamond).

The invention encompasses structurally novel 1-[(2'-substituted)-piperazin-1'-yl]-isoquinoline compounds that possess potent and selective binding affinity for the norpeinephrine transporter (NET) target protein found in peripheral and central nervous system tissues. The compounds of the invention are with novel chemical structures distinct from other NET inhibitor binding drugs and agents. The compounds of the invention are found with pharmacologically potent binding at the NET in various tissues, including brain. The compounds possess high selectivity for the NET protein relative to other competing drug binding sites in tissues. The compounds of the invention can be used in the treatment or prophylaxis of diseases and disorder characterized by NET or NE abnormalities.

The compounds of the invention can comprise one of the following structures,

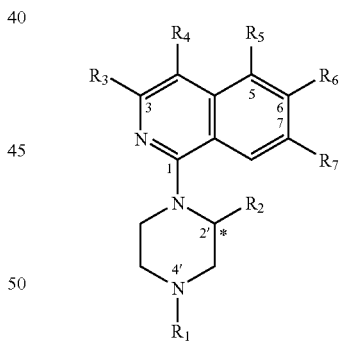

wherein, * independently denotes an R or S configuration or a racemic mixture; and wherein $R_1$ can be H, methyl, alkyl, or halo-alkyl; and further wherein $R_2$ and $R_3$ are independently selected from H, halogen, alkyl (straight chain or branched), O-alkyl, S-alkyl, aryl-alkyl-, halo-substituted-alkyl-, halo-substituted-alkenyl-, substituted-alkenyl-, alkyl-oxy-alkyl ether-, halo-substituted-alkyl-oxy-alkyl ether-, aryl-oxy-alkyl ether-, O-aryl, S-aryl, amino, amino-alkyl, or amino-aryl; and further wherein $R_4$, $R_5$, $R_6$, and $R_7$ are independently selected from H, halogen, alkyl (straight chain or branched), O-alkyl, halo-substituted-alkyl-, halo-substituted-alkenyl-, substituted-alkenyl-, carboxyl acid, or carboxylic ester, nitro, amino, or substituted-amino. The $R_1$-$R_7$ atomic and functional group definitions of the compounds of the invention are defined as standard atom and group classifications known within the art [Smith & March 2001].

The invention encompasses radioactive tracer forms of the compounds, which have radioactive atoms bonded to them to facilitate in vivo and in vitro imaging detection and quantification methods. The chemical attachment of positron emitting atoms, and similar radionuclides, to certain forms of the agents and at select regiochemical locations affords radioligands (tracers).

The tracer compounds of the invention can comprise one of the following structures,

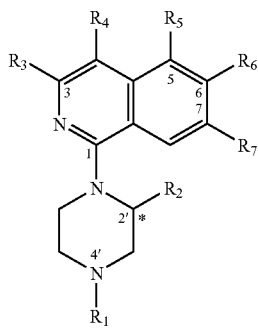

wherein, * independently denotes an R or S configuration or a racemic mixture; and wherein $R_1$ can be H, methyl, alkyl, halo-alkyl, $^3H$, $^{18}F$, or $^{11}C$; and further wherein $R_2$ and $R_3$ are independently selected from H, halogen, alkyl (straight chain or branched), O-alkyl, S-alkyl, aryl-alkyl-, halo-substituted-alkyl-, halo-substituted-alkenyl-, substituted-alkenyl-, alkyl-oxy-alkyl ether-, halo-substituted-alkyl-oxy-alkyl ether-, aryl-oxy-alkyl ether-, O-aryl, S-aryl, amino, amino-alkyl, amino-aryl, $^3H$, $^{18}F$, $^{75}Br$, $^{76}Br$, $^{123}I$, $^{124}I$, $^{125}I$, $^{131}I$, or $^{11}C$; and further wherein $R_4$, $R_5$, $R_6$, and $R_7$ are independently selected from H, halogen, alkyl (straight chain or branched), O-alkyl, halo-substituted-alkyl-, halo-substituted-alkenyl-, substituted-alkenyl-, carboxyl acid, carboxylic ester, $^3H$, $^{18}F$, $^{75}Br$, $^{76}Br$, $^{123}I$, $^{124}I$, $^{125}I$, $^{131}I$, or $^{11}C$. The $R_1$-$R_7$ atomic and functional group definitions of the radiotracers of the invention are defined as standard atom and group classifications known within the art [Smith & March 2001].

The radioligands are imaging tracers that detect and quantify NET densities within live and post-mortem tissues, including brain. The term tissue means a part of a subject's or patient's body. The tissue imaging methods encompass positron emission tomography (PET), single photon emission computed tomography (SPECT) and autoradiography. For live tissue imaging, preferably the radiotracers of the invention can be administered to subjects in an amount suitable for in vivo imaging thereof, and to locate, diagnose identify evaluate detect and quantify NET in CNS diseases and disorders, without limitation including anxiety, depression, attention deficit disorder, drug dependency, post traumatic stress disorder, and neurodegenerative disorders co-morbid with abnormalities of NET and/or NE. Generally, a unit dosage comprising a radiotracer of the invention may vary depending on subject or patient considerations. Such considerations include for example, age, condition, sex, extent of disease, contraindications, or concomitant therapies.

The compounds of the invention may also be administered to a subject or patient with other therapeutic agents that may be useful in the treatment of a CNS disease, disorder, condition or malady characterized by anxiety, depression, attention deficit disorder, drug dependency, post traumatic stress disorder and neurodegenerative conditions co-morbid with abnormalities of NET and/or NE. A method is provided for administering an effective amount of one or more compounds of the invention to a subject suffering from or believed to be at risk of suffering from a disease or disorder characterized by NET or NE abnormalities. The method also comprises administering either sequentially or in combination with one or more compounds of the invention a conventional therapeutic measure protocol or agent that can potentially be effective for the treatment or prophylaxis of a NET or NE system disease or disorder.

The compounds and radiotracers of the invention also include analogs, salts, compositions, derivatives, pro-drugs and discrete configurational stereochemical constitutions (racemic mixtures or enantiomeric stereochemical forms) thereof. A pharmaceutically acceptable salt refers to an acid or base salt of a compound or radiotracer of the invention, which possesses the desired pharmacological activity and is neither biologically nor otherwise undesirable.

Administration of a compound or radiotracer of the invention to a subject may be local or systemic and accomplished orally, intradermally, intramuscularly, subcutaneously, intravenously, intraaterially or intrathecally (by spinal fluid); or via powders, ointments, drops or as a buccal or nasal spray. A typical composition for administration can comprise a pharmaceutically acceptable carrier for the compound or radiotracer of the invention. Pharmaceutically acceptable carrier include, without limitation, aqueous solutions, non-toxic excipients comprising salts, preservative or buffers, amongst others known within the art.

In one embodiment, a composition can also comprise a pharmaceutically acceptable carrier and compound or radiotracer of the invention. A composition of the invention can be administered to a subject by conventional techniques including, without limitation, by a bolus injection.

The invention provides methods for syntheses of compounds and radiotracers of the invention. Within some embodiments, some starting material reagents for the syntheses are prepared by established procedures [Bedurftig 2006 & 2004, Naylor 1993] and use several procedures to join piperazine addends to isoquinoline fragments, including a lithium amide coupling methodology adapted from a procedure of Gilman [1945].

EXAMPLE I

Synthesis, Scheme 1.

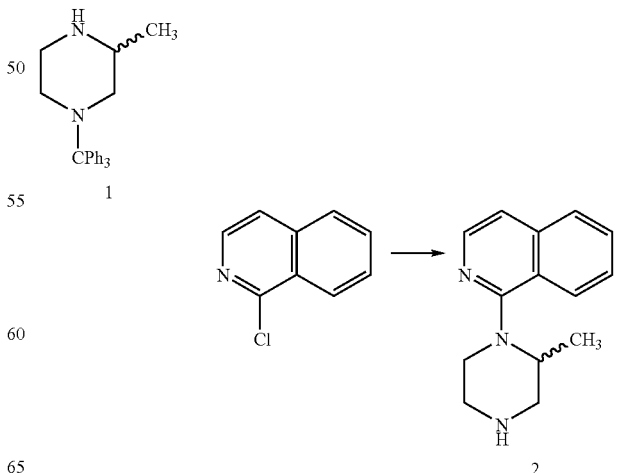

(±)-1-[2'-(Methyl)piperazin-1'-yl]isoquinoline, 2

To a 0° C. solution of triphenylmethyl-piperazine 1 [Gerdes 2000] (0.508 g, 1.67 mmol) in dry ether (20 mL) under argon was added (dropwise) n-butyllithium (2.3 M in hexane, 1.5 mmol). After stirring for 20 min, a solution of 1-chloro isoquinoline (0.186 g, 1.13 mmol) in ether (5 mL) was added (drop-wise) and the solution allowed to stir for 20 min at 0° C. then at ambient temperature for 1 h. The reaction was diluted with ether (10 mL), washed with saturated NaHCO$_3$ (25 mL) and brine (15 mL), the organic portion was dried (K$_2$CO$_3$) and concentrated to give the crude material that was partially purified by column chromatography (silica gel, EtOAc:hexanes, 1:3) to provide a the coupled product that was not characterized and immediately subjected to trityl group deprotection. To a suspension of coupled product intermediate in 20 mL of 95% ethanol was added HCl (6 M, 6 mL). The homogenous solution was stirred at ambient temperature for 30 min and the reaction contents were transferred to a separation funnel and diluted with 100 mL of saturated NaHCO$_3$. The aqueous phase was extracted with CH$_2$Cl$_2$ (4×20 mL) and the combined extracts were treated with di-tert-butyldicarbonate (0.257 g, 1.13 mmol) and stirred 10 minutes. The reaction was dried (K$_2$CO$_3$) and the solvent evaporated to provide a crude N-Boc intermediate that was purified by column chromatography (silica gel, EtOAc:hexanes, 1:3) to provide a 0.72 g of a purified N-Boc intermediate that was immediately deprotected. The N-Boc intermediate was dissolved in 6 mL of THF cooled to 0° C. and treated with H$_2$SO$_4$ (4 M, 6 mL) and additional H$_2$SO$_4$ (18 M, 0.25 mL). After 10 min the reaction contents were poured into 10 mL of 3 M NaOH solution and further diluted with 25 mL of saturated NaHCO$_3$. The aqueous mixture was extracted with CH$_2$Cl$_2$ (4×15 mL) and the combined extracts were dried (K$_2$CO$_3$) and concentrated to provide compound 2 as a pale oil (0.305 g, 82% overall yield). $^1$H NMR (400 MHz, CDCl$_3$): δ 1.05 (d, J=6.2 Hz, 3H), 2.32 (bs, 1H), 2.85 (m, 1H), 3.05-3.22 (m, 3H), 3.29 (m, 1H), 3.40-3.48 (m, 1H), 3.85 (m, 1H) 7.31 (d, J=5.9 Hz, 1H), 7.53 (t, J=7.7 Hz, 1H), 7.63 (t, J=7.6 Hz, 1H), 7.77 (d, J=8.2 Hz, 1H), 8.25-8.65 (m, 2H). HRMS Calcd. for [C$_{14}$H$_{17}$N$_3$+H$^+$]: 228.1501. Found 228.1502.

EXAMPLE II

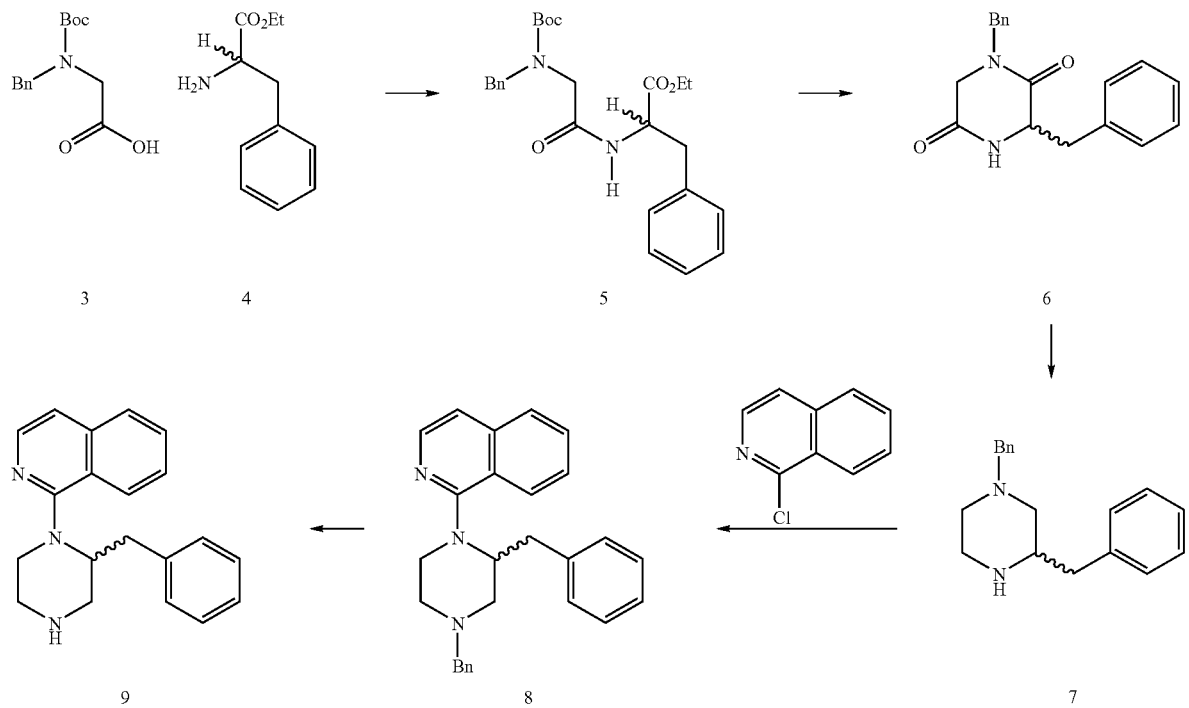

Synthesis, Scheme 2.

(±)-N-tert-Butoxycarbonyl-N-benzylglycyl-phenylalanine Methyl Ester, 5

To a stirring suspension of 1-[3-(dimethylamino)propyl]-3-ethylcarbodiimide hydrochloride (1.15 g, 6 mmol) in reagent grade CH$_2$Cl$_2$ (20 mL) was added a solution of pentafluorophenol (1.5 g, 8.1 mmol) in CH$_2$Cl$_2$ (10 mL) followed by a solution of N-Boc-N-Benzyl glycine 3 [Naylor 1993] (1.32 g, 5.0 mmol) in CH$_2$Cl$_2$ (20 mL). The solution was stirred at ambient temperature for 1 h then triethylamine (2.5 mL, 18 mmol) was added with additional CH$_2$Cl$_2$ (10 mL). The (±)-phenylalanine methyl ester hydrochloride (1.32 g, 5 mmol) was then added in small portions. The final solution was stirred for 20 h at ambient temperature and then was washed with aqueous sodium carbonate (1 M, 100 mL), aqueous citric acid (1 M, 100 mL) and water (50 mL). The organic phase was dried (K$_2$CO$_3$) and concentrated to afford the crude product. Column chromatography of the crude material (silica gel, EtOAc:hexanes, gradient 1:3 3:2) to provided 5 as a clear viscous oil (2.17 g, 102%, solvent heavy). $^1$H NMR (400 MHz, CDCl$_3$): δ 1.45 (s, 9H), 2.99-3.16 (bm, 2H), 3.72 (s, 3H), 3.79 (bd, J=16.1 Hz, overlapped with bm, 2H), 4.30-4.50 (bm, 2H), 4.85 (m, 1H), 6.27 (bs, 0.3H), 6.63 (bs, 0.3H), 7.05-7.11 (bm, 2H), 7.17-7.34 (m, 8H); $^{13}$C NMR (100 MHz, CDCl$_3$): δ 28.2, 37.8, 50.2, 51.2 (v. broad), 52.3, 52.8 (broad), 81.1, 127.1, 127.6, 128.1 (broad), 128.6, 129.1, 135.6, 136.9, 155.3 (broad), 168.9 (broad), 171.5.

(±)-1,3-Dibenzylpiperazine-2,5-dione, 6

To a 0° C. solution of dipeptide 5 (2.18 g, 5.11 mmol) in methanol (30 mL) was slowly added excess thionyl chloride (1.9 mL). The solution stirred at ambient temperature for 2.5 h. The solvent was evaporated and the residue was triturated with ~30 mL of ether, producing a white solid that was collected by filtration. The solid was dissolved in methanol (40 mL) and treated with ammonium hydroxide (29%, 10 mL) and then stirred for 18 h followed by concentration. The solid residue was partitioned between saturated NaHCO$_3$ (40 mL), water (20 mL) and CHCl$_3$:isopropyl alcohol, 4:1 (40 mL). The organic phase was separated and the aqueous phase extracted with CHCl$_3$:isopropyl alcohol, 4:1 (3×40 mL). The combined organic phases were dried (K$_2$CO$_3$) and concentrated to afford 6 as a white solid (1.382 g, 92% yield). $^1$H NMR (400 MHz, CDCl$_3$): δ 2.99 (d, part of AB pattern, J=17.6 Hz, $^1$H), 3.17 (m, AB pattern, 2H), 3.52 (d, part of AB pattern, J=17.6 Hz, 1H), 4.35 (m, 1H), 4.48 (m, AB pattern, J=14.7 Hz, 1H), 6.39 (bs, NH, 1H), 7.13-7.35 (m, 10H, overlapped with CDCl$_3$); $^{13}$C NMR (100 MHz, CDCl$_3$): δ 40.5, 48.2, 49.6, 56.4, 127.4, 128.1, 128.59, 128.63, 128.8, 130.0, 134.65, 134.68, 165.2, 166.3.

(±)-1,3-Dibenzylpiperazine, 7

To a 0° C. suspension of dione 6 (1.38 g, 4.7 mmol) in dry THF (120 mL) was added LiAlH$_4$ (0.713 g, 18.8 mmol) in two portions. The mixture was maintained on ice for 15 min, then the reaction was heated at reflux for 2.5 h. The solution was cooled and stirred for an additional 19 h then the excess LiAlH$_4$ was quenched by the careful, sequential addition of 0.7 mL water, 1.3 mL 4 M NaOH and 0.7 mL water. The solids that formed will filtered (Celite) and the filtrate concentrated to provide 7 as a pale colored solid (1.29 g, 103%, with THF) that slowly formed from an oil. $^1$H NMR (400 MHz, CDCl$_3$): δ 1.93 (m, triplet shape, 1H), 2.11 (td, J=2.9, 11.0 Hz, 1H, overlapped with bs, NH, 1H), 2.58 (dd, 8.8, 13.2 Hz, 1H), 2.70-2.77 (m, 2H), 2.79-2.87 (m, 2H), 2.92 (dt, J=2.3, 11.7 Hz, 1H), 3.02 (m, 1H), 3.51 (dd, AB pattern, J=12.8 Hz, 2H), 7.18-7.33 (m, 10H); $^{13}$C NMR (100 MHz, CDCl$_3$): δ 40.7, 45.6, 53.3, 56.2, 59.6, 63.3, 126.3, 127.0, 128.1, 128.4, 129.2, 137.9, 138.5. HRMS Calcd. for [C$_{18}$H$_{22}$N$_2$+H$^+$]: 267.1861. Found 267.1869.

(±)-1-[2',4'-(Dibenzyl)piperazin-1'-yl]isoquinoline, 8

Compound 7 (0.067 g, 0.252 mmol) in dry diethyl ether (5 mL) was cooled (0° C.) and then treated with n-butyl lithium (0.252 mmol). The resultant solution was stirred for 20 minutes, then 1-chloroisoquinoline (0.027 g, 0.168 mmol) dissolved in dry diethyl ether (~2 mL) added, The mixture was allowed to stir at 0° C. for 20 min and gradually warmed to room temperature and stirred for 16 h. The reaction was quenched with 5 mL sat. sodium bicarbonate solution, diluted with ether (30 mL) transferred to a separation funnel and the organic portion was washed with brine. The organic portion was dried (K$_2$CO$_3$) and the solvent evaporated to give a yellow crude oil. Purification of the oil by chromatography (silica gel, EtOAc:hexanes, 3:17) afforded coupled product 8 as a clear oil (0.016 g, 24% yield) which was used directly in the following reaction. HRMS Calcd. for [C$_{27}$H$_{27}$N$_3$+H$^+$]: 394.2283. Found 394.2244.

(±)-1-[2'-(Benzyl)piperazin-1'-yl]isoquinoline, 9

Compound 8 (0.014 g, 0.036 mmol) was dissolved in dry 1,2-dichloroethane (2 mL). To the solution was added 1-chloroethyl chloroformate (0.01 ml, 0.093 mmol) in a drop-wise fashion and then the reaction mixture was refluxed for 3 hours. The reaction was allowed to cool overnight and the volatiles were removed in vacuo. The residue was treated with methanol (~5 mL) and heated at reflux for 1 h. The methanol was removed under reduced pressure and the residue was dissolved in 1N HCl (5 mL) and washed with diethyl ether (20 mL). The aqueous portion was made basic (pH>8) with 4N NaOH, diluted with saturated sodium bicarbonate solution and extracted with dichloromethane (4×10 mL). The combined organic portions were dried (K$_2$CO$_3$), filtered, and the solvent removed under reduced pressure to afford a crude brown oil. Purification of the oil by chromatography (silica gel, elution with two solvent systems: first EtOAc:hexanes, 3:2, then MeOH:CH$_2$Cl$_2$, 3:17) provided compound 9 as a clear oil (0.004 g, 37% yield). $^1$H NMR (400 MHz, CDCl$_3$): δ 2.43 (br s, 1H), 2.79-2.94 (m, 2H), 2.94-3.05 (m, 1H), 3.05-3.26 (m, 3H), 3.26-3.40 (m 1H), 3.45-3.64 (m, 1H), 4.08 (m, 1H), 7.01 (m, 2H), 7.06-7.20 (m, 3H), 7.28 (d, J=5.9 Hz, 1H0, 7.49 (t, J=7.7 Hz, 1H), 7.61 (t, J=7.7 Hz, 1H), 7.76 (d, J=8.1 Hz, 1H), 8.21 (d, J=5.9 Hz, 1H). HRMS Calcd. for [C$_{20}$H$_{21}$N$_3$+H$^+$]: 304.1814. Found 304.1433.

EXAMPLE III

Synthesis, Scheme 3.

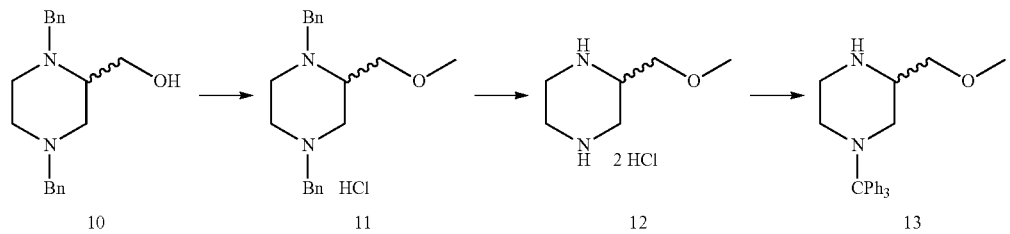

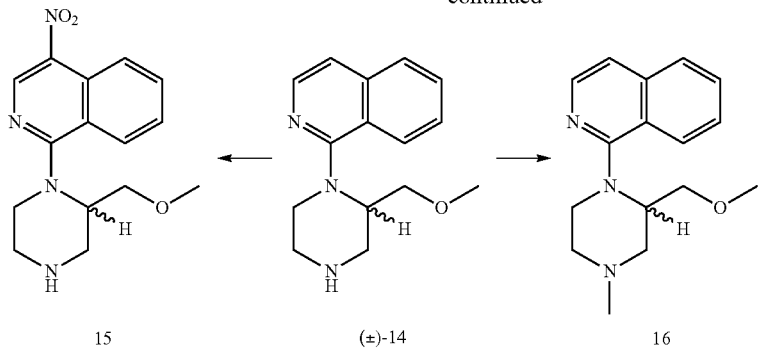

15      (±)-14      16

(±)-1,4-Dibenzyl-2-methoxymethylpiperazine, 11

Compound 10 [Rondeau 1997] (3.97 g, 13.4 mmol) was dissolved in dry DMF (40 mL) and cooled to 0° C. To the solution was added NaH (0.96 g, 40.2 mmol) to give a turbid white suspension, which was stirred for 20 min. Iodomethane (2.29 g, 16.1 mmol) was added to the suspension solution. The reaction was allowed to stir at 0° C. for 20 min, then at room temperature for 3 hours. The reaction was quenched by the addition of water (50 mL). The aqueous phase of the mixture was extracted with $Et_2O$ (3×50 ml), the organic portions were combined, dried ($K_2CO_3$), and concentrated in vacuo to give a tan oil. The oil was purified by column chromatography (silica gel, EtOAc:hexanes, 1:3) to give 11 as a clear oil (3.4 g, 82%). The oil was dissolved in ether (300 ml) and HCl gas was bubbled through the solution, giving a fine white precipitate. The solids were collected by filtration, washed with ether and dried in vacuo to afford the hydrochloride salt of 11 as a white powder (4.06 g, 79% yield). Free base: $^1$H NMR (400 MHz, $CDCl_3$): δ 2.28 (m, 3H), 2.61 (dd, 1H), 2.77 (m, 3H), 3.35 (s, 3H), 3.54 (d, 3H), 3.62 (d, 1H), 3.64 (d, 1H), 7.25-7.5 (m, 10H). HRMS Calcd. for $[C_{20}H_{26}N_2O+H^+]$: 311.2123. Found 311.1894.

(±)-2-Methoxymethylpiperazine dihydrochloride, 12

Compound 11 (4.06 g, 10.6 mmol) was dissolved in methanol (100 ml). To the stirred solution was added 5% palladium on carbon (0.61 g) and the flask was sealed with a septum. A hydrogen balloon was attached and the gas was bubbled through the solution while stirring vigorously. The reaction was stirred for 2 hours. The reaction mixture was filtered over a pad of celite rinsing with MeOH, this was concentrated in vacuo to give 12 as a white solid (2.14 g, 98% yield), which was used directly in the next reaction. HRMS Calcd. for $[C_6H_{16}Cl_2N_2O+H^+]$: 203.0718. Found 203.1653.

(±)-2-Methoxymethyl-4-triphenylmethlpiperazine, 13

Compound 12 (2.14 g, 10.5 mmol) was dissolved in dry $CH_2Cl_2$ (60 ml), in the presence of dry triethylamine (5.9 ml, 42.3 mmol). The solution was cooled (0° C.) and triphenylmethyl chloride (2.94 g, 10.6 mmol) in dry $CH_2Cl_2$ (10 ml) was added drop-wise. Once the addition was complete the reaction was warmed to room temperature and stirred for 16 h. The reaction mixture was washed with saturated $NaHCO_3$ (75 mL), water (75 mL), and brine (75 mL). The organic portion was dried ($K_2CO_3$), and concentrated in vacuo to give 13 as an amorphous foam (3.96 g, 99% yield). $^1$H NMR (400 MHz, $CDCl_3$): δ 1.3 (m, 3H), 1.9 (s, 3H), 3.0 (m, 3H), 3.2 (m, 1H), 3.3 (s, 3H), 7.16 (m, 4H), 7.27 (m, 7H), 7.49 (m, 4H).

(±)-1-[2'-(Methoxymethyl)piperazin-1'-yl] isoquinoline, 14

To a 0° C. solution of compound 13 (0.545 g, 1.46 mmol) in dry ether (20 mL) under argon was added (drop-wise) n-butyllithium (2.3 M in hexane, 1.46 mmol) producing a slightly colored turbid solution. After stirring for 20 min, a solution of 1-chloroisoquinoline (0.160 g, 0.97 mmol) in ether (5 mL) was added (drop-wise) and the solution allowed to stir for 20 min at 0° C. then at ambient temperature for 14 h. The reaction was diluted with ether (10 mL), washed with saturated $NaHCO_3$ (2×25 mL) and brine (1×25 mL), dried ($K_2CO_3$) and concentrated to give a crude material that was purified by column chromatography (silica gel, EtOAc:hexanes, 1:3). The crude material was not characterized and immediately subjected to 10 mL of 95% ethanol to which was added HCl (6 M, 6 mL). The solution was stirred at ambient temperature for 30 min and the reaction was diluted with 100 mL of saturated $NaHCO_3$. The aqueous phase of the mixture was extracted with $CH_2Cl_2$ (4×20 mL) and the combined organic extracts were treated with di-tert-butyldicarbonate (0.316 g, 1.44 mmol) and stirred 10 minutes. The crude reaction solution was dried ($K_2CO_3$) and then the solvent evaporated to provide a crude N-Boc intermediate that was partially purified by column chromatography (silica gel, EtOAc:hexanes, 1:3). The N-Boc intermediate was dissolved in 6 mL of THF and cooled to 0° C. To the stirring solution was added $H_2SO_4$ (4 M, 6 mL) and additional $H_2SO_4$ (18 M, 0.25 mL). After 10 min the reaction contents were poured into 10 mL of 3 M NaOH solution and further diluted with 25 mL of saturated $NaHCO_3$. The aqueous mixture was extracted with $CH_2Cl_2$ (4×15 mL) and the combined extracts were dried ($K_2CO_3$) and concentrated to provide 14 as a pale oil (0.1058 g, 42% overall yield). $^1$H NMR (400 MHz, $CDCl_3$): δ 2.34 (bs, 1H), 3.01-3.13 (m, 3H), 3.15 (s, 3H), 3.26-3.33 (m, 2H), 3.42-3.54 (m, 2H), 3.67 (dd, J=7.7, 9.4 Hz, 1H), 3.99 (m, 1H) 7.24 (d, J=5.8 Hz, 1H), 7.47 (m, 1H), 7.57 (m, 1H), 7.72 (d, J=8.1 Hz, 1H), 8.12-8.16 (m, 2H); $^{13}$C NMR (100 MHz, $CDCl_3$): 46.0, 47.1, 48.3, 57.3, 58.8, 70.4, 116.0, 122.3, 125.5, 126.1, 126.9, 129.6, 138.2, 140.5, 161.2. HRMS Calcd. for $[C_{15}H_{19}N_3O+H^+]$: 258.1606. Found 258.1407.

The formation of a salt composition of 14 was synthesized by dissolving 14 (0.023 g, 0.091 mmol) in dry ether (0.25 mL), and treating the solution with an aliquot of dry ether saturated with dry HCl gas. The resultant white precipitate was collected as the HCl salt of 14 (0.025 g, 92% yield), which is considered a pharmaceutically acceptable salt.

(±)-1-[2'-(Methoxymethyl)piperazin-1'-yl]-4-nitroisoquinoline, 15

Compound 14 (0.020 g, 0.078 mmol) was dissolved in $H_2SO_4$ (0.25 mL) and cooled to 0° C. A solution of potassium nitrate (0.0083 g, 0.082 mmol) dissolved in H$_2$SO$_4$ (0.25 mL) was added to the cooled reaction solution. The reaction mixture was stirred (0° C.) for 40 min then ice was added. The mixture made basic (pH=9) with 4 N NaOH, diluted with saturated NaHCO$_3$ (2 mL), and extracted with CH$_2$Cl$_2$ (4×30 mL). The organic portions were combined, dried (K$_2$CO$_3$), filtered and the solvent was removed under reduced pressure to afford 0.018 g of a crude orange oil. Purification of the oil by chromatography (silica gel, MeOH:CH$_2$Cl$_2$, 1:20) provided compound 15 as a yellow-orange oil (0.008 g, 32% yield). $^1$H NMR (400 MHz, CDCl$_3$): δ 1.73 (br s, 1H), 2.94-3.22 (m, 3H), 3.27 (s, 3H), 3.61-3.73 (m, 2H), 3.74-3.91 (m, 2H), 3.94-4/03 (m, 1H), 4.64 (m, 1H), 7.54 (t, J=7.7 Hz, 1H), 7.79 (t, J=8.1 Hz, 1H), 8.07 (d, J=8.1 Hz, 1H), 8.81 (d, J=8.1 Hz, 1H), 9.06 (s, 1H).

(±)-1-[2'-(Methoxymethyl)-4'-methyl-piperazin-1'-yl]isoquinoline, 16

Compound 14 (0.034 g, 0.132 mmol) was dissolved in MeOH (1.5 mL). To the solution was added 10% palladium on charcoal (0.010 g) followed by 0.1 mL of formalin. The mixture was stirred at room temperature, flushed with hydrogen gas, and stirred 14 h over 1 atm of H$_2$ gas. The solution was filtered (Celite) and the solvent was removed under reduced pressure to provide compound 16 as a pale yellow oil 0.034 g, 96% yield). $^1$H NMR (400 MHz, CDCl$_3$): δ 2.34 (s, 3H), 2.40-2.49 (m, 1H), 2.60-2.68 (m, 1H), 2.74-2.84 (m, 2H), 3.15 (s, 3H), 3.39-3.62 (m, 3H), 3.69 (m, 1H), 4.12 (m, 1H), 7.20-7.29 (m, 1H), 7.47 (t, J=7.7 Hz, 1H), 7.58 (t, J=7.3 Hz, 1H), 7.72 (d, J=8.1 Hz, 1H), 8.09-8.17 (m, 2H); $^{13}$C NMR (100 MHz, CDCl$_3$): δ 46.6, 47.0, 55.3, 56.4, 57.5, 58.9, 70.8, 115.8, 122.2, 125.6, 126.1, 127.0, 129.6, 138.2, 140.5, 161.0. HRMS Calcd. for [C$_{16}$H$_{21}$N$_3$O+H$^+$]: 272.1763. Found 272.1686.

EXAMPLE IV

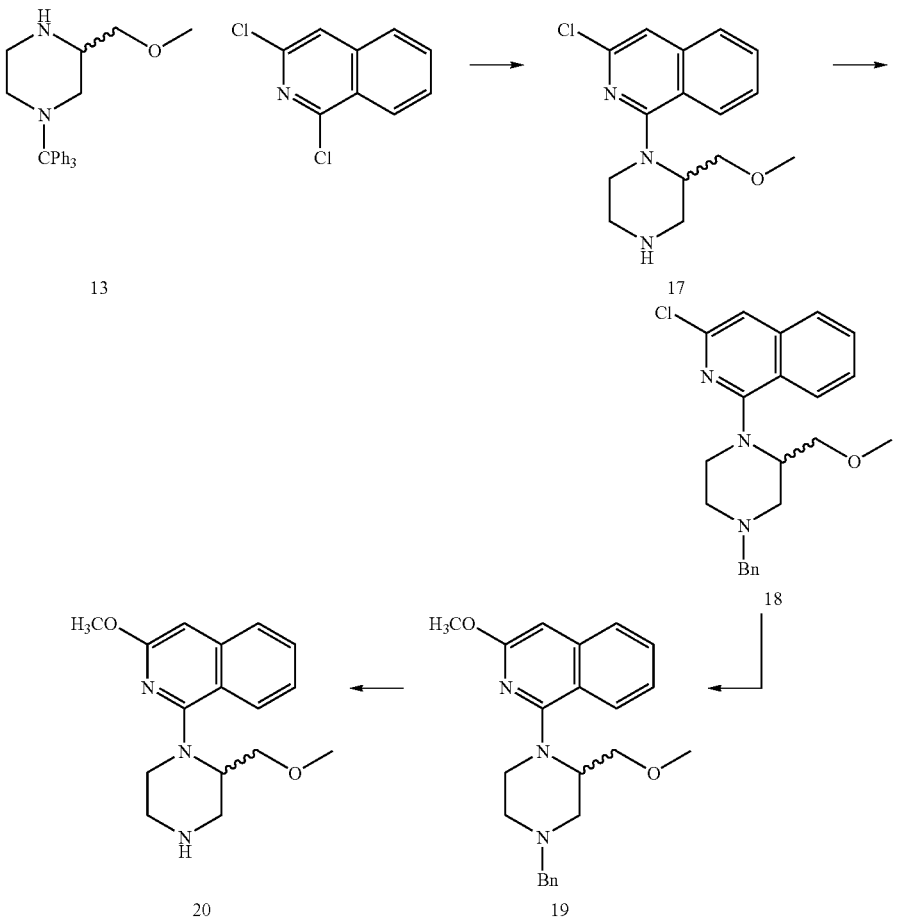

Synthesis Scheme 4.

(±)-3-Chloro-1-[2'-(methoxymethyl)piperazin-1'-yl]isoquinoline, 17

A solution of compound 13 (1.00 g, 2.685 mmol) in dry ether (15 mL) was cooled to 0° C. and then n-butyllithium (2.685 mmol) was added. The mixture was stirred for 20 min at 0° C. and then 1,3-dichloroisoquinoline (0.354 g, 1.79 mmol) in dry ether (~2 mL) was added to the mixture. The reaction was allowed to warm to room temperature, stirred for 14 h, and then quenched with saturated NaHCO$_3$ (5 mL). The mixture was diluted with ether, transferred to a separation funnel and washed with brine. The organic portion wash dried (K$_2$CO$_3$), filtered and solvent removed in vacuo to provide a crude yellow foam. Purification of the foam by chromatography (silica gel, EtOAc:hexanes, 1:4) afforded 0.909 g of the intermediate coupled material, which was used directly in the next transformation. The coupled material was dissolved in 20 mL of THF and treated with 6 N HCl (10 mL). The mixture was stirred at room temperature for 20 min then the solvent was removed under reduced pressure. The residue was dissolved in 1 N HCl, washed with ether (2×20 mL), then made basic (pH>8) with 4 N NaOH additional with dilution with NaHCO$_3$ and extracted with CH$_2$Cl$_2$ (3×70 mL). The organic portions were combined, dried (K$_2$CO$_3$), filtered and the solvent was removed in vacuo to provide 17 as a tan oil (0.326 g, 63% yield). $^1$H NMR (400 MHz, CDCl$_3$): δ 3.39 (s, 3H), 3.41-3.62 (m, 3H), 3.75-3.89 (m, 3H), 3.89-4.01 (m, 1H), 4.01-4.10 (m, 1H), 4.32 (m, 1H), 7.34 (s, 1H), 7.50 (t, J=7.3 Hz, 1H), 7.62 (t, J=7.7 Hz, 1H), 7.68 (d, J=8.1 Hz, 1H), 7.98 (d, J=8.1 Hz, 1H); $^{13}$C NMR (100 MHz, CDCl$_3$): 45.3, 46.3, 47.2, 57.0, 59.3, 70.9, 114.2, 120.4, 125.8, 126.3, 126.6, 130.7, 140.3, 143.3, 160.9. HRMS Calcd. for [C$_{15}$H$_{18}$ClN$_3$O+H$^+$]: 292.7839. Found 292.1222.

(±)-1-[4'-Benzyl-2'-(methoxymethyl)piperazin-1'-yl]-3-chloroisoquinoline, 18

A solution of compound 17 in CH$_2$Cl$_2$ (2 mL) was treated with benzyl bromide (0.06 mL, 0.491 mmol) and the reaction mixture was stirred at room temperature for 12 h. The solvent was removed under reduced pressure and the resulting residue was purified by chromatography (silica gel, EtOAc:hexanes, 1:4) to provide 18 as a clear oil (0.138 g, 81% yield). $^1$H NMR (400 MHz, CDCl$_3$): δ 2.39-2.52 (m, 1H), 2.53-2.63 (m, 1H), 2.77-2.92 (m, 2H), 3.18 (s, 3H), 3.45-3.72 (m, 5H), 3.73-3.81 (m, 1H), 4.22 (br s, 1H), 7.21 (s, 1H), 7.22-7.38 (m, 5H), 7.41 (t, J=7.3 Hz, 1H), 7.56 (t, J=7.3 Hz, 1H), 7.63 (d, J=8.1 Hz, 1H), 8.1 (d, J=8.1 Hz, 1H). HRMS Calcd. for [C$_{22}$H$_{24}$ClN$_3$O+H$^+$]: 382.1686. Found 382.1362.

(±)-1-[4'-Benzyl-2'-(methoxymethyl)piperazin-1'-yl]-3-methoxyisoquinoline, 19

A solution of compound 18 (0.129 g, 0.338 mmol) in dry DMF (~5 mL) was treated with sodium methoxide (0.182 g, 3.38 mmol) as one portion. The mixture was allowed to stir overnight at 150° C. An additional 500 mol percent of sodium methoxide and 0.05 g of anhydrous K$_2$CO$_3$ were added and the mixture was heated for another 2 h. The mixture was cooled and the solvent removed under reduced pressure. The resulting residue was dissolved in CH$_2$Cl$_2$ and filtered, then dried (K$_2$CO$_3$), filtered and solvent removed under reduced pressure to afford a crude oil. The oil was purified by chromatography (silica gel, EtOAc:hexanes, gradient 1:20 to 3:17) to afford 19 as a clear colorless oil (0.013 g, 10% yield). $^1$H NMR (400 MHz, CDCl$_3$): δ 1.61 (br s, 1H), 2.45-2.55 (m, 1H), 2.57-2.65 (m, 1H), 2.75-2.89 (m, 2H), 3.20 (s, 3H), 3.48-3.69 (m, 5H), 3.76-3.83 (m, 1H), 3.94 (s, 3H), 4.21 (m, 1H), 6.53 (s, 1H), 7.18-7.29 (m, 1H), 7.29-7.40 (m, 5H), 7.45 (t, J=7.3 Hz, 1H), 7.59 (d, J=8.8 Hz, 1H), 8.02 (d, J=8.1 Hz, 1H). HRMS Calcd. for [C$_{23}$H$_{27}$N$_3$O$_2$+H$^+$]: 378.4873. Found 378.2154.

(±)-3-Methoxy-1-[2'-(methoxymethyl)piperazin-1'-yl]isoquinoline, 20

A solution of compound 19 (0.011 g, 0.029 mmol) in dry methanol (10 mL) within a Parr pressure flask was treated with 10% palladium on charcoal (0.050 g). The pressure flask was shaken under 55 psi of H$_2$ gas for 6 h. The solution was filtered through a pad of Celite and the solvent was removed under reduce pressure. The crude residue was dissolved in 1 N HCl (10 mL), washed with CH$_2$Cl$_2$ (2×10 mL), then made basic (pH>8) with 4 N NaOH, and diluted with saturated NaHCO$_3$. The aqueous portion was extracted with CH$_2$Cl$_2$ (4×20 mL), the organic portions were combined, dried (K$_2$CO$_3$), filtered, and the solvent was removed in vacuo to afford a crude oil. The oil was purified by chromatography (silica gel, eluted first with EtOAc:hexane, 3:2 then methanol:CH$_2$Cl$_2$, 3:17) to provide 20 as a clear colorless oil (0.005 g, 60% yield). $^1$H NMR (400 MHz, CDCl$_3$): δ 1.85 (br s, 1H), 3.06-3.20 (m, 3H), 3.25 (s, 3H), 3.26-3.35 (m, 1H), 3.44-3.52 (m, 1H), 3.52-3.62 (m, 2H), 3.80 (m, 1H), 3.95 (s, 3H), 4.11 (m, 1H), 6.56 (s, 1H), 7.21-7.29 (m, 1H), 7.47 (t, J=7.7 Hz, 1H), 7.61 (d, J=8.1 Hz, 1H), 8.00 (d, J=8.8 Hz, 1H). HRMS Calcd. for [C$_{16}$H$_{21}$N$_3$O$_2$+H$^+$]: 288.1746. Found 288.1568.

EXAMPLE V

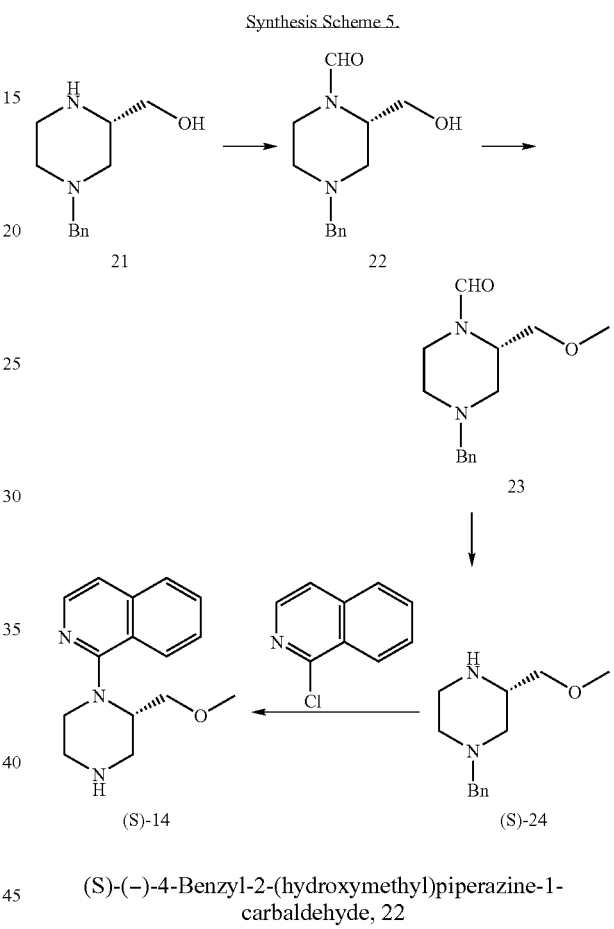

Synthesis Scheme 5.

(S)-(−)-4-Benzyl-2-(hydroxymethyl)piperazine-1-carbaldehyde, 22

To a 0° C. solution of the alcohol 21 [Naylor 1993] (0.567 g, 2.75 mmol) in formic acid (88%, 8 mL) was added (dropwise) acetic anhydride (2.33 mL, 24.7 mmol). The reaction was stirred for 30 min at 0° C. then warmed to ambient temperature. After 1 h the reaction was diluted with ice, placed back in an ice bath and made basic with 4 N NaOH (~50 mL). The aqueous mixture was further diluted with saturated NaHCO$_3$ (30 mL) and extracted with CH$_2$Cl$_2$ (4×20 mL). The combined extracts were dried (K$_2$CO$_3$) and concentrated to give an orange-brown oil that was purified by column chromatography (silica gel, MeOH:CHCl$_3$, gradient 1:199 to 1:49) to afford 22 as a pale colored oil (0.521 g, 67% yield). $^1$H NMR (400 MHz, CDCl$_3$): δ 2.05 (td, J=3.7, 11.7 Hz, 0.5H), 2.13 (td, J=3.7, 11.7 Hz, 0.5H), 2.28 (dd, J=4.0, 11.7 Hz, 1H), 2.87 (m, 1H), 2.90-3.02 (m, 1H), 3.12 (td, J=4.0, 12.8 Hz, 0.5H), 3.41-3.59 (m, 3.5H), 3.64-3.75 (m, 1H), 3.85 (m, 0.5H), 3.97 (dd, J=5.5, 11.4 Hz, 0.5H), 4.08 (dd, J=7.3, 11.4 Hz, 0.5H), 4.20 (bd, 0.5H), 4.38 (m, 0.5H), 7.25-7.36 (m, 5H), 8.06 (s, 0.5H), 8.08 (s, 0.5H); $^{13}$C NMR (100 MHz, CDCl$_3$): δ 37.3, 43.9, 49.1, 52.1, 52.9, 54.36, 54.44, 55.5, 62.7, 62.8, 63.6, 65.2, 127.5, 127.6, 128.4, 128.5, 128.8, 128.9, 136.8, 137.2, 161.8, 161.9; (R)-[α]$_D^{25}$ +56.1 (c 0.050, CHCl$_3$). HRMS Calcd. for [C$_{13}$H$_{18}$N$_2$O$_2$+H$^+$]: 235.1447. Found 235.1446. [α]$_D^{25}$ −53.8 (c 0.052, CHCl$_3$).

(S)-(−)-4-Benzyl-2-(methoxymethyl)piperazine-1-carbaldehyde, 23

To a 0° C. solution of alcohol 22 (0.502 g, 2.14 mmol) in dry DMF (20 mL) was added NaH (95%, 0.154 g, 6.43 mmol) in one portion. After stirring 5 min, iodomethane (0.319 g, 2.25 mmol) was added (drop-wise) and the mixture stirred for 20 min at 0° C. then at ambient temperature for 1.5 h. The excess NaH was destroyed by the careful addition of water and the solution was diluted with 40 mL each of water and saturated NaHCO$_3$. The aqueous mixture was extracted with ether (2×40 mL) and ethyl acetate (2×40 mL). The combined extracts were washed with brine (50 mL), dried (K$_2$CO$_3$) and concentrated to give a brown oil that was purified by column chromatography (silica gel, MeOH:CHCl$_3$, gradient 1:199 to 1:49) to afford 23 as a pale colored oil (0.360 g, 69% yield). $^1$H NMR (400 MHz, CDCl$_3$): δ 2.00-2.12 (m, 1.3H), 2.18 (dd, J=3.7, 11.7 Hz, 0.7H), 2.80-2.92 (m, 2H), 2.93-3.02 (m, 1H), 3.29-3.38 (m, 3H), 3.41-3.76 (m, 5H), 4.16 (bd, 0.7H), 4.60 (m, 0.3H), 7.25-7.35 (m, 5H), 8.04 (s, 0.7H), 8.07 (s, 0.3H); $^{13}$C NMR (100 MHz, CDCl$_3$): δ 36.7, 42.7, 47.0, 52.3, 53.2, 53.7, 54.1, 58.8, 59.0, 62.5, 62.6, 69.5, 70.6, 127.2, 128.3, 128.7, 137.7, 161.3, 161.9. HRMS Calcd. for [C$_{14}$H$_{20}$N$_2$O$_2$+H+] 249.1603. Found 249.1598. [α]$_D^{25}$ −37.6 (c 0.036, CHCl$_3$).

(S)-(+)-1-Benzyl-3-(methoxymethyl)piperazine, 24

A solution of the protected methylether 23 (0.320 g, 1.29 mmol) in THF (3 mL) and 4 M H$_2$SO$_4$ (9 mL) was heated at 55° C. for 5 h. After cooling, the reaction contents were poured into 20 mL of cold (−10° C.) 4 M NaOH and diluted with 20 mL of saturated NaHCO$_3$. The mixture was extracted with CH$_2$Cl$_2$ (4×15 mL) and the combined extracts dried (K$_2$CO$_3$) and concentrated to provide 24 as a pale oily solid (0.274 g, 96% yield). This product was of adequate purity for the subsequent transformations. $^1$H NMR (400 MHz, CDCl$_3$): δ 1.85 (t, J=10.3 Hz, 1H), 2.11 (td, J=3.3, 11.0 Hz, 1H), 2.35 (bs, 1H, NH), 2.74 (m, 2H, triplet shape), 2.90 (m, 1H, td shape), 2.96-3.06 (m, 2H), 3.25-3.36 (m, 5H, OCH$_3$ singlet present at 3.33), 3.50 (m, AB pattern, J=13.2 Hz, 2H), 7.22-7.33 (m, 5H); $^{13}$C NMR (100 MHz, CDCl$_3$): δ 45.2, 53.8, 54.4, 55.9, 59.0, 63.4, 75.1, 126.9, 128.1, 129.1, 138.0. HRMS Calcd. for [C$_{13}$H$_{20}$N$_2$O+H+] 221.1654. Found 221.1654. [α]$_D^{25}$ +14.4 (c 0.030, CHCl$_3$).

(S)-1-[2'-(Methoxymethyl)piperazin-1'-yl]isoquinoline, (S)-14

To a 0° C. solution of compound 24 (0.065 g, 0.295 mmol) in dry ether (10 mL) under argon was added (drop-wise) n-butyllithium (0.295 mmol) producing a slightly colored turbid solution. After stirring for 10 min, a solution of 1-chloroisoquinoline (0.032 g, 0.197 mmol) in ether (5 mL) was added (drop-wise) and the solution allowed to stir for 1 h at 0° C. then at ambient temperature for 14 h. The reaction was quenched with saturated NaHCO$_3$, diluted with ether and washed with saturated NaHCO$_3$ and then with brine. The organic portion was dried (K$_2$CO$_3$), filtered and concentrated to give a crude gold oil that was purified by column chromatography (silica gel, EtOAc:hexanes, 3:17). The acquired benzyl protected intermediate (HRMS Calcd. for [C$_{22}$H$_{25}$N$_3$O+H$^+$] 348.2076. Found 221.1654) was immediately used in the next transformation. The benzyl protected coupled intermediate (0.015 g, 0.043 mmol) was dissolved in dry 1,2-dichloroethane (1 mL). To the solution was added 1-chloroethyl chloroformate (0.01 mL, 0.093 mmol, neat) in a drop-wise fashion and then the reaction mixture was refluxed for 5 h. The mixture was cooled overnight and the volatiles were removed under reduced pressure. The residue was treated with methanol (~5 mL) and heated at reflux for 1 h. The methanol was removed under reduced pressure and the residue was dissolved in 1N HCl (2 mL) and washed with ether (15 mL). The aqueous portion was made basic (pH>8) with 4N NaOH, diluted with saturated NaHCO$_3$ solution and extracted with CH$_2$Cl$_2$ (3×10 mL). The combined organic portions were dried (K$_2$CO$_3$), filtered, and the solvent removed under reduced pressure to afford (S)-14 as a clear oil (0.004 g, 36% yield). HRMS Calcd. for [C$_{15}$H$_{19}$N$_3$O+H$^+$]: 258.1606. Found 258.1557. The $^1$H NMR was identical to compound (O)-14 of Example III.

In a similar way, the Scheme 5 synthesis may also employ the (R)-enantiomer of starting material 21 [Naylor 1993] thereby affording the opposing enantiomer of the final product, for example (R)-14.

EXAMPLE VI

Synthesis, Scheme 6.

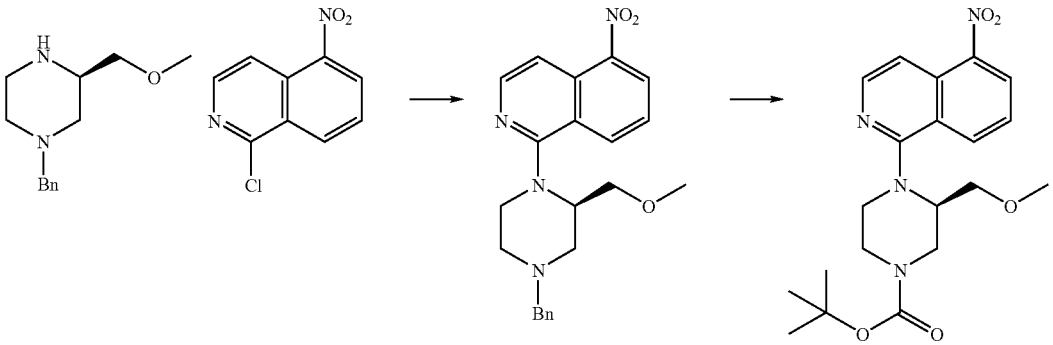

(R)-24  25  26  29

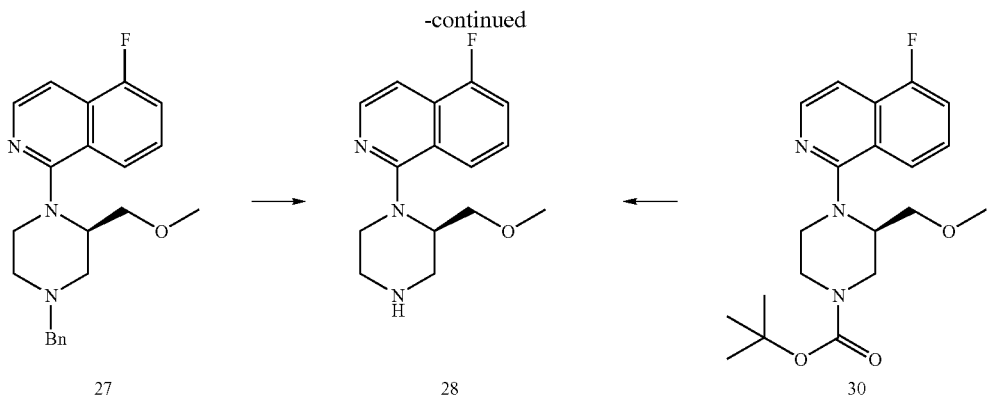

(R)-1-[4'-Benzyl-2'-(methoxymethyl)piperazin-1'-yl]-5-nitroisoquinoline, 26

The (R)-enantiomer of 24 ((R)-24) starting material was available by the method of Naylor [1993] utilizing L-serine. Starting material 25 was prepared according to literature methods [Robinson 1947]. A solution of (R)-24 (0.120 g, 0.545 mmol) in dry DMF (1.5 mL) was treated with compound 25, then heated at 130° C. for 1.5 h, then 145° C. 1 h, and finally at 150° C. for 1.5 h. The solvent was removed under reduced pressure and the residue was purified by chromatography (silica gel, EtOAc:hexanes, gradient 1:20 to 3:17) to afford 26 as a yellow oil (0.034 g, 16% yield). $^1$H NMR (400 MHz, CDCl$_3$): δ 1.66 (br s, 1H), 2.43-2.62 (m 2H), 2.79-2.91 (m, 2H), 3.14 (s, 3H), 3.46-3.75 (m 6H), 4.08 (m, 1H), 7.23-7.38 (m, 5H), 7.52 (t, J=8.1 Hz, 1H), 7.93 (d, J=5.9 Hz, 1H), 8.30 (d, J=5.9 Hz, 1H), 8.38 (d, J=8.8 Hz, 1H), 8.50 (d, J=8.8 Hz, 1H); $^{13}$C NMR (100 MHz, CDCl$_3$): δ 53.0, 54.0, 58.9, 59.0, 62.3, 70.8, 109.8, 122.6, 124.0, 127.1, 127.6, 128.3, 128.9, 131.1, 132.8, 138.2, 144.2, 145.4, 161.6. HRMS Calcd. for [C$_{22}$H$_{24}$N$_4$O$_3$+H$^+$]: 393.1927. Found 393.0805.

(R)-1-[4'-Benzyl-2'-(methoxymethyl)piperazin-11'-yl]-5-fluoroisoquinoline, 27

A solution of compound 26 (0.025 g, 0.064 mmol) in dry DMF (1 mL) was treated with dry tetramethylammonium fluoride (0.089 g, 0.957 mmol). The mixture was heated at 140° C. for 1 h, and then at 150-155° C. for 1.5 h. The mixture was cooled, diluted with CH$_2$Cl$_2$ (100 mL), filtered and the solvent was removed under reduced pressure. The resultant residue was purified by chromatography (silica gel, EtOAc: hexanes, 3:17) to afford compound 27 as a pale blue oil (0.010 g, 43% yield). $^1$H NMR (400 MHz, CDCl$_3$): δ 1.61 (br s, 1H), 2.45-2.56 (m, 1H), 2.56-2.66 (m, 1H), 2.85 (br d, J=11.0 Hz, 1H), 3.14 (s, 3H), 3.43-3.67 (m, 5H), 3.67-3.76 (m, 1H), 4.14 (m, 1H), 7.20-7.29 (m, 1H), 7.29-7.42 (m, 5H), 7.44 (d, J=5.9 Hz, 1H), 7.90 (d, J=8.8 Hz, 1H), 8.18 (d, J=5.9 Hz, 1H). HRMS Calcd. for [C$_{22}$H$_{24}$N$_3$O+H$^+$]: 366.1982. Found 366.1617.

(R)-1-[2'-(Methoxymethyl)piperazin-1'-yl]-5-fluoroisoquinoline, 28 from 27

A solution of compound 27 (0.010 g, 0.0274 mmol) in 1,2-dichloroethane (10 mL) was treated with 1-chloroethyl chloroformate (0.006 mL, 0.0548 mmol) at 25° C. and stirred for 5 min. The reaction mixture was heated to reflux and stirred for 2 h, then allowed to cool to room temperature and stirred for 14 h. The solvent was removed under reduced pressure and the residue was diluted with MeOH (10 mL). The solution was heated at reflux for 2 h, then cooled and the solvent was removed in vacuo. The resulting residue was dissolved in 1 N HCl (2 mL), washed with CH$_2$Cl$_2$ (2 mL), then the aqueous portion was made basic (pH=9) with 4 N NaOH and diluted with saturated NaHCO$_3$ (15 mL). The aqueous mixture was extracted with CH$_2$Cl$_2$ (4×10 mL), the organic portions were combined, dried (K$_2$CO$_3$), filtered and the solvent was removed under reduced pressure to afford compound 28 as a pale blue oil (0.0044 g, 59% yield). $^1$H NMR (400 MHz, CDCl$_3$): δ 1.68 (br s, 1H), 3.03-3.15 (m, 3H), 3.17 (s, 1H), 3.26-3.32 (m, 1H), 3.35 (dt, J=1.5, 3.7 Hz, 1H), 3.46-3.56 (m, 2H), 3.70 (m, 1H), 4.02 (m, 1H), 7.23-7.30 (m, 1H), 7.41 (m, 1H), 7.47 (d, J=5.9 Hz, 1H), 7.92 (d, J=8.1 Hz, 1H), 8.21 (d, J=5.9 Hz, 1H). HRMS Calcd. for [C$_{15}$H$_{18}$FN$_3$O+H$^+$]: 276.1512. Found 276.1268.

(R)-1-[4'-(tert-Butoxycarbonyl)-2'-(methoxymethyl)piperazin-1'-yl]-5-nitroisoquinoline, 29

A solution of compound 26 (0.013 g, 0.033 mmol) in 1,2-dichloroethane (3 mL) was treated with 1-chloroethyl chloroformate (0.02 mL, 0.166 mmol). The mixture was stirred at 25° C. for 5 min then heated at reflux for 4 h followed by room temperature for 14 h. The solvent was removed under reduced pressure and the residue was dissolved in methanol (5 mL) and the mixture was heated at reflux for 2 h. The solvent was removed in vacuo to afford a crude residue. The residue was dissolved in CH$_2$Cl$_2$ (3 mL) and treated with di-tert-butyldicarbonate (0.011 g, 0.050 mmol) and the reaction mixture was stirred at 25° C. for 14 h. The solvent was removed under reduced pressure and the yellow crude material was purified by chromatography (silica gel, EtOAc:hexanes, gradient 1:20 to 1:4) to afford compound 29 as a yellow oil (0.008 g, 60% yield). $^1$H NMR (400 MHz, CDCl$_3$): δ 1.49 (s, 9H), 3.21 (br s, 3H), 3.29-3.61 (br m, 6H), 3.91-4.17 (br m, 3H), 7.57 (t, J=8.1 Hz, 1H), 7.98 (d, J=6.7 Hz, 1H), 8.31 (d, J=5.9 Hz, 1H), 8.40 (d, J=8.1 Hz, 1H), 8.50 (br s, 1H). HRMS Calcd. for [C$_{20}$H$_{26}$N$_4$O$_5$+H$^+$]: 403.4522. Found 403.2345.

(R)-1-[4'-(tert-Butoxycarbonyl)-2'-(methoxymethyl)piperazin-1'-yl]-5-fluoroisoquinoline, 30

Compound 29 (0.031 g, 0.077 mmol) was dissolved in dry DMF and dry tetramethylammonium fluoride (0.100 g, 1.07 mmol) was added to the solution. The reaction vessel was lowered into a 130° C. heating bath. The heating bath was allowed to climb to 160° C. over 2 h, then the reaction was terminated by cooling and then dilution with CH$_2$Cl$_2$ (75 mL). The solution was filtered and the solvent removed under reduced pressure to provide a crude oil. Purification of the crude material by chromatography (silica gel, EtOAc:hexanes, 1:5.7) provided compound 30 as a clear oil (0.010 g, 35% yield). $^1$H NMR (400 MHz, CDCl$_3$): δ 1.49 (s, 9H), 2.93-3.06 (m, 1H), 3.21 (br s, 1H), 3.24-3.38 (m, 1H) 3.44 (s, 3H), 3.45-3.59 (m, 2H), 3.94-4.04 (m, 1H), 4.06 (m, 1H), 7.25-7.31 (m, 1H), 7.37-7.47 (m, 1H), 7.49 (t, J=7.3 Hz, 1H), 7.85-7.98 (m, 1H), 8.19 (dd, J=5.9, 5.9 Hz, 1H). HRMS Calcd. for [$C_{20}H_{26}FN_3O_3$+H$^+$]: 376.2036. Found 376.0355.

(R)-1-[2'-(Methoxymethyl)piperazin-1'-yl]-5-fluoroisoquinoline, 28 from 30

Compound 30 (0.003 g, 0.008 mmol) was treated with conc. $H_2SO_4$ (0.5 mL). The mixture was heated at ~50° C. for 20 min then cooled to room temperature and ice was added. The resultant solution was made basic (pH=10) with 4 N NaOH, diluted with saturated NaHCO$_3$ (2 mL), and extracted with CH$_2$Cl$_2$ (4×20 mL). The organic portions were combined, dried (K$_2$CO$_3$), filtered and the solvent removed in vacuo to afford 28 as a clear oil (0.002 g, 73% yield). The spectroscopic analyses of the product were identical to those acquired from the transformation of 27 to 28.

EXAMPLE VII

(R)-1-Benzyl-3-((tetrahydro-2H-pyran-2-yloxy)methyl)piperazine-2,5-dione, 32

To a 0° C. suspension of compound 31 [Naylor 1993] (0.913 g, 3.90 mmol) in dry CH$_2$Cl$_2$ (40 mL) under argon was added dihydropyran (1.64 g, 19.5 mmol) followed by p-toluenesulfonic acid monohydrate (0.025 g, 0.13 mmol). After 30 minutes the reaction was poured into an aqueous mixture of 30 mL each of saturated NaHCO$_3$, brine and water. The organic phase was separated and the aqueous phase extracted with (3×15 mL). The combined organic extracts were dried (K$_2$CO$_3$) and concentrated giving ~2 g of crude material. The crude material was dissolved in 20 mL CH$_2$Cl$_2$ and 4 g of silica gel was added. The mixture was concentrated and the residue was chromatographed (silica gel, MeOH:CH$_2$Cl$_2$, gradient 1:39 to 1:19) to provide compound 32 as a white solid (1.153 g, 93% yield). $^1$H NMR (400 MHz, CDCl$_3$): δ 1.40-1.70 (m, 6H), 3.50 (m, 1H), 3.69-3.77 (m, 2H), 3.79-3.85 (m, 1H), 3.92 (s, 0.6H), 3.96 (s, 0.4H), 4.05 (dd, J=2.9, 9.9 Hz, 0.4H), 4.12 (dd, J=5.5, 10.3 Hz, 0.6H), 4.23 (m, 1H), 4.33 (d, J=14.7 Hz, 0.4H), 4.38 (d, J=14.7 Hz, 0.6H), 4.62 (m, 1H), 4.83 (d, J=14.7 Hz, 0.6H), 4.90 (d, J=14.7 Hz, 0.4H), Synthesis, Scheme 7.

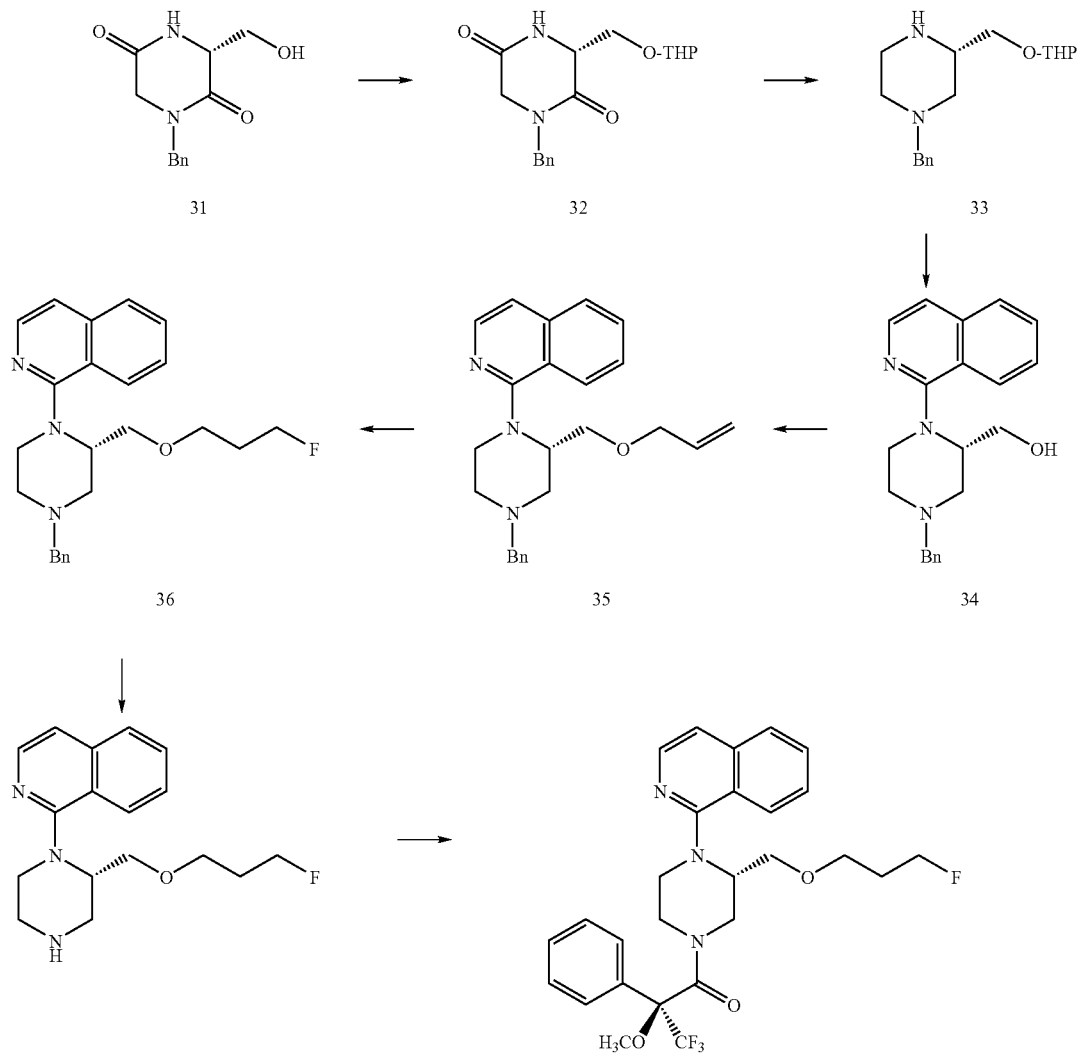

6.41 (bs, 0.4H, NH), 6.52 (bs, 0.6H, NH), 7.24-7.36 (m, 5H); $^{13}$C NMR (100 MHz, CDCl$_3$): δ 18.9, 19.0, 25.1, 30.1, 30.2, 49.2, 49.3, 49.7, 49.8, 55.9, 62.0, 62.1, 69.5, 69.8, 98.9, 99.1, 128.1, 128.2, 128.5, 128.8, 128.9, 135.0, 164.4, 164.6, 166.0, 166.3. HRMS Calcd. for [C$_{17}$H$_{22}$N$_2$O$_4$$^+$H$^+$]: 319.1658. Found 319.1649.

(S)-1-Benzyl-3-[(tetrahydro-2H-pyran-2-yloxy)methyl]piperazine, 33

To a 0° C. suspension of compound 32 (1.153 g, 3.62 mmol) in dry THF (60 mL) on ice was added LiAlH4 (0.566 g, 14.89 mmol). The mixture was then heated at reflux for 2 h. The solution was cooled, stirred 1 h then the excess LiAlH$_4$ was quenched by the sequential addition of 0.6 mL water, 1.2 mL 4 M NaOH solution and 0.6 mL water. The solids that formed will filtered (Celite) and the filtrate concentrated to give 33 as a pale colored oil (1.076 g, 99% yield). $^1$H NMR (400 MHz, CDCl$_3$): δ 1.44-1.62 (m, 4H), 1.64-1.74 (m, 1H), 1.74-1.94 (m, 2H), 2.08-2.17 (m, 1H), 2.35 (bs, 1H, NH), 2.71-2.79 (m, 2H), 2.87-2.95 (m, 1H), 2.95-3.08 (m, 2H), 3.26 (m, 0.5H), 3.36 (dd, J=4.0, 9.9 Hz, 0.5H), 3.45-3.52 (m, 3H), 3.61-3.73 (m, 1H), 3.78-3.86 (m, 1H), 4.56 (m, 1H); $^{13}$C NMR (100 MHz, CDCl$_3$): δ 19.4, 19.5, 25.3, 30.5, 45.1, 53.4, 53.5, 54.5, 54.7, 55.7, 62.2, 62.4, 63.3, 69.5, 69.9, 98.8, 99.5, 127.0, 128.2, 129.1, 137.9.

(S)-1-[4'-Benzyl-(2'-hyroxymethyl)piperazin-1'-yl]isoquinoline, 34

Compound 33 (0.300 g, 0.001 mol) in dry ether (15 mL) was cooled to 0° C. and treated with n-butyllithium (0.0011 mol). The mixture was stirred at 0° C. for 15 min then a solution of 1-chloroisoquinoline (0.168 g, 0.001 mol) in ether (5 mL) was added. The reaction mixture was brought to room temperature and stirred for 14 h. The reaction was quenched with saturated NH$_4$Cl (10 mL) and extracted with EtOAc (3×50 mL). The organic extracts were combined, washed with water (30 mL) then dried (K$_2$CO$_3$). The solution was filtered and the solvent removed under reduced pressure to provide a crude oil. Purification of the crude material chromatography (silica gel, EtOAc:hexane, 1:3) afforded 0.198 g (43%) of the coupled intermediate which was used directly in the next reaction. The intermediate (0.198 g, 0.5 mmol) was dissolved in methanol (15 mL) and treated with concentrated HCl (0.1 mL). The mixture was stirred at room temperature for 3 h, then the solvent removed under reduced pressure. The residue was suspended in EtOAc (30 mL) and then treated with added saturated NaHCO$_3$ (20 mL). The organic portion was collected, dried (K$_2$CO$_3$), filtered and concentrated to provide the alcohol 34 as a pale yellow oil (0.216 g, 94% yield). $^1$H NMR (400 MHz, CDCl$_3$): δ 2.62 (m, 2H), 2.85 (m, 2H), 3.50-3.78 (m, 5H), 4.10 (m, 1H), 4.36 (m, 1H), 6.32 (br s, 0.5H, OH), 7.21 (d, J=5.9 Hz, 1H), 7.22-7.40 (m, 5H), 7.49 (t, J=7.6 Hz, 1H), 7.61 (t, J=7.7 Hz, 1H), 7.74 (d, J=8.1 Hz, 1H), 8.02 (d, J=5.9 Hz, 1H), 8.06 (d, J=8.0 Hz, 1H).

(S)-1-[4'-Benzyl-(2'-allyloxymethyl)piperazin-1'-yl]isoquinoline, 35

To a 0° C. solution of the alcohol 34 (0.158 g, 0.474 mmol) in dry DMF (15 mL) was added sodium hydride (0.043 g, 1.42 mmol). The turbid solution was stirred 15 min then allyl bromide (0.086 g, 0.711 mmol) was added. The reaction was stirred 10 min at 0° C. then warmed to ambient temperature and stirred for 14 h. The excess hydride was destroyed by the careful addition of 8 mL of saturated NaHCO$_3$ solution and the mixture diluted further with 8 mL of water. This aqueous mixture was extracted with ether (4×15 mL) and the combined extracts were washed with brine (2×10 mL), dried (K$_2$CO$_3$) and concentrated to give the crude product that was purified by column chromatography (silica gel, EtOAc:Hexanes, 1:4) to provide 35 as a pale yellow oil (0.10 g, 56% yield). $^1$H NMR (400 MHz, CDCl$_3$): δ 2.53 (td, J=12.5, 3.4 Hz, 1H), 2.66 (dd, J=3.3, 12.6 Hz, 1H), 2.90 (br m, 2H), 3.42-3.55 (m, 3H), 3.59-3.70 (m, 3H), 3.72-3.86 (m, 3H), 4.17 (br s, 1H), 4.99-5.07 (m, 2H), 5.61-5.572 (m, 1H), 7.21 (d, J=5.9 Hz, 1H), 7.22-7.41 (m, 5H), 7.46 (t, J=7.6 Hz, 1H), 7.57 (t, J=7.8 Hz, 1H), 7.72 (d, J=7.7 Hz, 1H), 8.14 (m, 2H).

(S)-1-[4'-Benzyl-2'-[(3-fluoropropoxyox)methyl]piperazin-1'-yl]isoquinoline, 36

To a 0° C. solution of compound 35 (0.060 g, 0.161 mmol) in dry THF (15 mL) was added 9-BBN (0.5 M in THF, 0.433 mmol). Following the addition, the reaction was heated to 60° C. and maintained for 1 h. The contents were cooled to 0° C. and 2.5 mL of 1 M NaOH was added (drop-wise) followed by an equal volume of 30% H$_2$O$_2$. After stirring ~10 min the THF was evaporated and the residue partitioned between CH$_2$Cl$_2$ and saturated NaHCO$_3$ (25 mL each). The organic phase was separated and the aqueous phase extracted with CH$_2$Cl$_2$ (3×15 mL). The combined organic extracts were dried (K$_2$CO$_3$) and concentrated to give the crude material that was purified by column chromatography (silica gel, EtOAc:hexanes, gradient 1:9 to 3:2) to afford the corresponding alcohol as an oil (0.062 g, 98% yield) which was used directly in the next reaction. To a −78° C. solution of the intermediate alcohol (0.062 g, 0.158 mmol) in dry CH$_2$Cl$_2$ (10 mL) was added diethylaminosulfur trifluoride (0.033 g, 0.206 mmol). The reaction mixture was allowed to stir and warm to ambient temperature over 16 h. The reaction mixture was diluted with CH$_2$Cl$_2$ (5 mL) and saturated NaHCO$_3$ solution (10 mL). The organic phase was separated and the aqueous phase extracted with CH$_2$Cl$_2$ (2×10 mL). The organic extracts were combined, dried (K$_2$CO$_3$), and concentrated to give the crude product that was purified by column chromatography (silica gel, EtOAc:hexanes, 1:4) to provide 36 as a pale oil (0.050 g, 80% yield). $^1$H NMR (400 MHz, CDCl$_3$): δ 1.64 (dp, J$_{F-H}$=25.6 Hz, FCH$_2$CH$_2$— J$_{H-H}$=6.2 Hz, 2H), 2.52 (td, J=12.5, 3.4 Hz, 1H), 2.63 (dd, J=12.6, 3.3 Hz, 1H), 2.81-293 (m, 2H), 3.23-3.36 (m, 2H), 3.42-3.51 (m, 2H), 3.57-3.74 (m, 4H), 4.09-4.20 (m, 2H), 4.22-4.31 (m, 1H), 7.21 (d, J=5.7 Hz, 1H), 7.22-7.39 (m, 5H), 7.47 (t, J=7.7 Hz, 1H), 7.58 (t, J=7.6 Hz, 1H), 7.72 (d, J=7.7 Hz, 1H), 8.15 (m, 2H).

(S)-1-[2'-[(3-fluoropropoxy)methyl]piperazin-1'-yl]isoquinoline, 37, and Amide 38

To a 0° C. solution of fluoride 36 (0.098 g, 0.249 mmol) in dry 1,2-dichloroethane (10 mL) was added 1-chloroethyl chloroformate (0.142 g, 0.994 mmol). After stirring 5 min, the reaction was heated at reflux for 2 h, cooled, then stirred at ambient temperature for 14 h. The volatile components were evaporated and the residue was dissolved in methanol (10 mL) and heated at 60° C. for 1.5 h. The solvent was evaporated to dryness and the residue partitioned between CH$_2$Cl$_2$ and saturated NaHCO$_3$ (10 mL each). The organic phase was separated and the aqueous phase was extracted with three additional portions of CH$_2$Cl$_2$. The combined organic extracts were dried (K$_2$CO$_3$) and concentrated to give the crude product that was immediately purified by column chromatography (silica gel, two step elution; EtOAc:Hexanes, 4:1 then MeOH:CH$_2$Cl$_2$ gradient 1:39-1:9) to provide 37 as a pale colored oil (0.030 g, 96% yield). $^1$H NMR (400 MHz, CDCl$_3$): δ 1.685 (dp, J$_{F-H}$=25.1 Hz, FCH$_2$CH$_2$— J$_{H-H}$=6.0 Hz, 2H), 3.41-3.62 (m, 8H), 3.65-3.80 (m, 3H), 3.84 (m, 1H), 4.14 (br m, 1H), 4.42 (dt, J$_{F-H}$=47.2 Hz, FCH$_2$, J$_{H-H}$=5.9 Hz, 2H), 7.30 (d, J=5.9 Hz, 1H), 7.52 (t, J=7.7 Hz, 1H), 7.62 (t, J=7.6 Hz, 1H), 8.08 (d, J=8.2 Hz, 1H), 8.14 (m, J=5.9 Hz, 1H); $^{13}$C NMR (100 MHz, CDCl$_3$): δ 30.8 (d, J$_{C-F}$=19 Hz, FCH$_2$CH$_2$—), 43.2, 44.2, 45.6, 55.1, 67.3, 69.5, 81.6 (d, J$_{C-F}$=163 Hz, FCH$_2$—), 117.4, 122.4, 125.1, 126.9, 127.7, 130.3, 138.4, 140.7, 160.0. HRMS Calcd. for [C$_{17}$H$_{22}$FN$_3$O+H$^+$]: 304.1825. Found 304.1819.

To evaluate stereochemical integrity of 37 the Mosher's amide was prepared [Hoye 1996]. A solution of 37 (0.020 g, 0.066 mmol), triethylamine (0.1 mL) in dry CH$_2$Cl$_2$ (10 mL) was treated with (R)-(+)-α-methoxy-α-trifluoromethylphenylacetic acid chloride (0.017 g, 0.067 mmol). The reaction mixture was stirred at room temperature for 14 h, then CH$_2$Cl$_2$ (5 mL) and saturated NaHCO$_3$ (15 mL) were added to the mixture. The organic portion was separated, dried (K$_2$CO$_3$), filtered, and the solvent was removed under reduced pressure to provide a crude residue. Purification of the residue by chromatography (silica gel, EtOAc:hexane, 1:4) provided the (2'S, 4'R)-diastereomeric amide 38 as a pale yellow oil (0.025 g, 73% yield). HRMS Calcd. for [C$_{27}$H$_{29}$F$_4$N$_3$O$_3$+H$^+$]: 520.2223. Found 520.1860. $^{13}$C NMR (100 MHz, CDCl$_3$): δ 30.7 (d, J$_{C-F}$=19.1 Hz, FCH$_2$CH$_2$—), 42.3, 43.8, 45.7, 47.0, 56.2, 57.0, 57.1, 66.4, 67.0, 68.8, 81.1 (d, J$_{C-F}$=163 Hz, FCH$_2$—), 117.0, 122.4, 122.9, 125.3, 126.7, 126.8, 127.3, 128.6, 128.7, 129.6, 130.2, 134.1, 138.4, 140.7, 160.6, 165.0. Analysis of the $^1$H NMR spectrum of 38 (400 MHz, CDCl$_3$) revealed the consistent stereochemical quality of 38 indicated by the methoxyl group chemical shift resonance found at δ 3.73.

In a similar way, the Scheme 7 synthesis may also employ the (S)-enantiomer of starting material 31 [Naylor 1993] thereby affording the opposing enantiomer of the final product, for example (R)-37. The racemic mixture (±)-37 is prepared in a similar way starting from D,L-serine [Naylor 1993].

EXAMPLE VIII

Tracer radiosynthesis, Scheme 8.

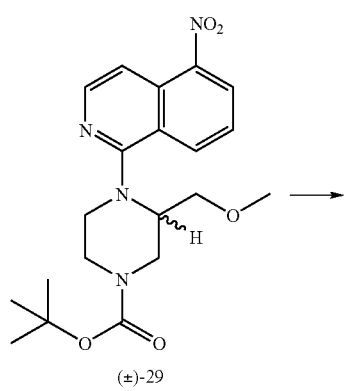

(±)-29

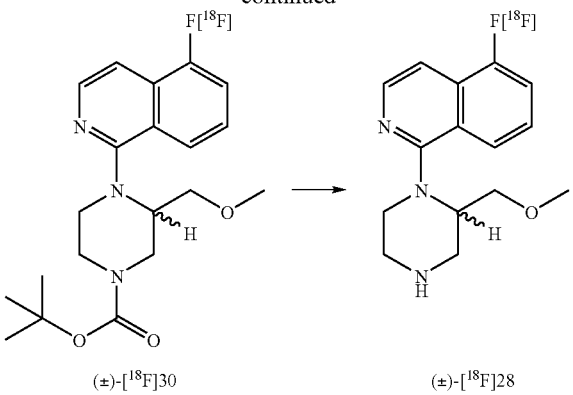

(±)-[$^{18}$F]30     (±)-[$^{18}$F]28

The Scheme 8 transformations serve as an example for high specific activity fluorine-18 ([$^{18}$F]) radiolabeling reactions to afford tracers of the invention. The Scheme 8 radiolabeling sequence is related to the chemical transformations described in Example VI. [$^{18}$F]Fluoride was produced with a Siemens RDS Eclipse cyclotron (Knoxville, Tenn.) using 95% enriched [$^{18}$O]water (Marshall Isotopes, Tel Aviv, Israel). 4,7,13,16,21,24-hexaoxa-1,10-diazabicyclo[8.8.8]-hexacosane (K222) was purchased from Sigma-Aldrich (St. Louis). Extra dry acetonitrile (ACN) and dimethyl formamide (DMF) were purchased from Acros Organics (Geel, Belgium). All other chemicals were reagent grade or better. Sep-Pak® Light C18 cartridges (Waters, Milford, Mass.), and [$^{18}$F]fluoride Trap and Release cartridges (ORTG, Oakdale, Tenn.) were used for solid phase extractions (SPE). [$^{18}$F] fluoride was loaded onto a trap and release column, eluted in K222 (5 mg)/K$_2$CO$_3$ (1 mg) in 95% ACN/5% water (v/v) (1 mL), dried under N$_2$ (g), dried by azeotropic distillation with ACN (3×1 mL) under N$_2$ (g), and dissolved in DMF (0.2 mL). Precursor (±)-29 (1.4 mg) in DMF (50 µL) was added to [$^{18}$F]fluoride (840 mCi) in DMF. The reaction was conducted in a sealed reaction vessel under N$_2$ (g) with stirring, at 170° C. for 50 min. The reaction solution containing (±)-[$^{18}$F]30 was diluted in water (20 mL) and loaded on a Sep Pak light C18 cartridge in order to trap (±)-[$^{18}$F]30 and elute unreacted [$^{18}$F]fluoride. The cartridge was washed in water (5 mL), and eluted in ethanol (2 mL) to recover (±)-[$^{18}$F]30. Mean decay corrected (DC) yield of the transformation of (±)-29 to crude (±)-[$^{18}$F]30 was 17%. Intermediate (±)-[$^{18}$F]30 was hydrolyzed with 2 M HCl (1 mL) in ethanol (~2 mL). The solution was heated at 140° C. under a stream of N$_2$ (g) until the mixture was reduced in volume to approximately 0.5 mL. The resultant mixture was neutralized with 2 M sodium acetate (1.5 mL).

Semi-preparative HPLC was performed on the neutralized solution, using a GP50 HPLC system (Dionex, Sunnyvale, Calif.) UV and radioactivity detectors, with a 10 mm×250 mm Jupiter 3 C-18 column (Phenomenex, Torrance, Calif.) eluted in solvent A, 0.1% trifluoroacetic acid. (aq) and solvent B, 0.01% trifluoroacetic acid in 90% ACN/10% water (v/v), with a gradient of 10% B to 90% B in 30 minutes at 3 mL per minute. The major radioactive peak containing (±)-[$^{18}$F]28 was collected ($t_R$ 13.5 min). The decay corrected yield of (±)-[$^{18}$F]30 to (±)-[$^{18}$F]28 was 57%.

Product (±)-[$^{18}$F]28 in ACN/water HPLC eluent (~1 mL) was diluted in water (20 mL) and loaded and trapped on a Sep Pak light C18 cartridge. The cartridge was washed in water (5 mL) to remove remaining ACN, and eluted in ethanol (~2 mL) to recover (±)-[$^{18}$F]28. Water (0.2 mL) was added to (±)-[$^{18}$F]28 in ethanol, and the solution was heated at 140° C. under a stream of $N_2$ (g) until reduced in volume to approximately 0.1 mL. The aqueous solution of (±)-[$^{18}$F]28 was then formulated in water and sodium acetate, to a final concentration of 8 mCi/mL in 0.1 M sodium acetate, pH 7, calibrated for injection time into trial subjects. The radiosynthesis, purification, and dose formulation time was ~2.5 h.

Analytical HPLC was performed with a Breeze HPLC system (Waters, Milford, Mass.) with a 4.6×250 mm Jupiter 2 C-18 column (Phenomenex, Torrance, Calif.), solvents A and B and gradient as above, at 1.5 mL per minute. Analytical HPLC was performed on small aliquots of formulated (±)-[$^{18}$F]28 (2 μL) with and without addition of an [$^{19}$F] product standard ((±)-28), and detected by radioactivity and UV (254 nm). Analytical HPLC demonstrated co-elution of (±)-[$^{18}$F]28 and the product standard (±)-28. To determine specific activity, a standard curve was constructed using the areas under the analytical HPLC 254 nm peak of (±)-28 product standard (0.000327 μmol and 0.00383 μmol). Product (±)-[$^{18}$F]28 was allowed to decay for a day, then aliquots equivalent to 1.2 to 2.6 mCi of formulated radiopharmaceutical were evaluated by analytical HPLC. The areas under the peak for (±)-[$^{18}$F]28 were interpolated against the standard curve to determine the mass of (±)-[$^{18}$F]28, from which specific activity was calculated. For example, the specific activity of tracer (±)-[$^8$F]28 at the time of injection was calculated as 730 mCi/μmol.

EXAMPLE IX

Tracer radiosynthesis, Scheme 9.

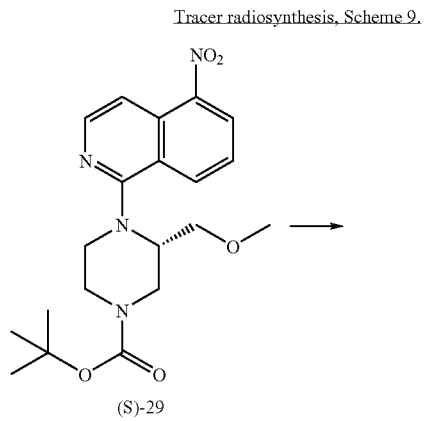

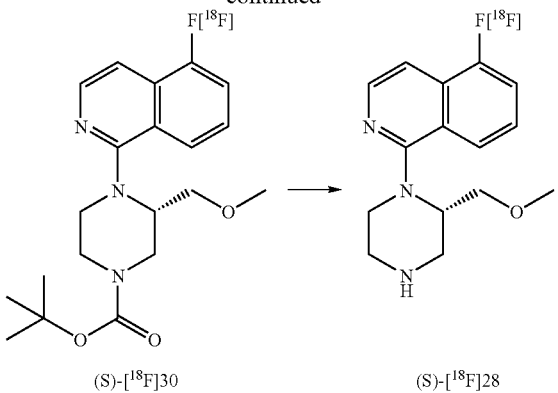

Using a method analogous to that described in Example VIII, the tracer (S)-[$^{18}$F]28 was prepared according to Scheme 9, in an overall decay corrected radiochemical yield of 14.7%, and specific activity of 1270 mCi/μmol, over a radiosynthesis, purification, and dose formulation time of ~2.5 h. Tracer saline dose formulations were made as per the method described in Example VIII.

EXAMPLE X

Compound Pharmacological Competitive Binding Potency at NET

The pharmacological inhibitory binding potency of the molecules of the invention for the NET protein have been measured as $K_i$ determinations employing a modified competition assay protocol similar to an established method described in the literature [Raisman 1982, Tejani-Butt 1992, Owens 1997]. In essence, the molecules of the invention $K_i$ values have been derived from $IC_{50}$ measures [Cheng 1973] with binding curves of 6-8 or more points of analog test drug concentrations from $1\times10^{-3}$ to $1\times10^{-12}$ M in competition with the known NET inhibitor drug agent [$^3$H]nisoxetine. The protocol employed partially purified rat brain cortical homogenates, [$^3$H]nisoxetine, incubated 0° C., 4 h; with nonspecific binding determined with added 1 microM of desipramine (DMI) and desipramine as the parallel positive control. Examples of the molecules of the invention that have been evaluated with the NET pharmacological assay are shown in Chart 1. The respective NET potencies reported as competitive binding $K_i$ values are summarized in Table 1, with desipramine as an established inhibitor drug binding standard measure. The molecules of the invention are found with competitive binding potencies at NET and are considered NET binding inhibitor agents.

TABLE 1

Chart 1

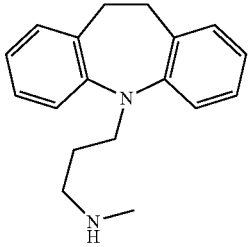

Desipramine (DMI)
Standard

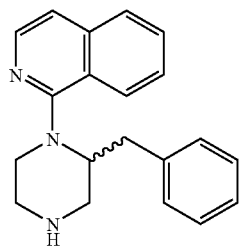

9

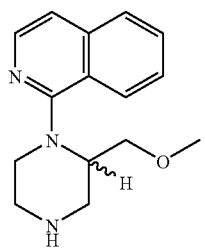

(±)-14

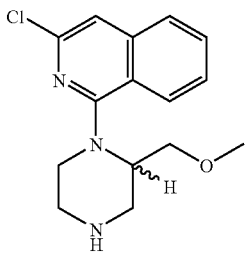

17

TABLE 1-continued

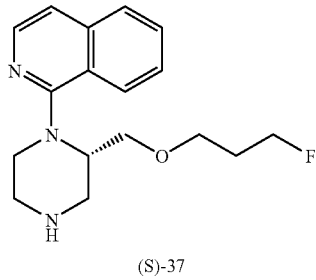

(S)-37

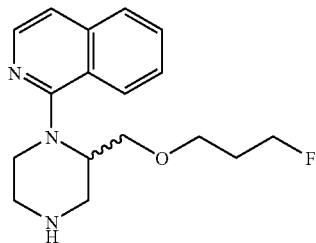

(±)-37

| Compound | NET $K_i$ (nM) |
|---|---|
| DMI (standard) | 0.71 |
| 9 | 16.2 |
| (±)-14 | 4.14 |
| 17 | 14.2 |
| (S)-37 | 6.71 |
| (±)-37 | 71.5 |

EXAMPLE XI

Compound Pharmacological CNS Selectivity

An example to demonstrate the pharmacological selectivity of the molecules of the invention for the NET protein relative to other competitive binding sites within the CNS is provided with compound (±)-14. The evaluation of the competitive binding affinities ($K_i$ values) of (±)-14 for the serotonin and dopamine transporter proteins (SERT and DAT, respectively), the beta-adrenergic receptor, and also serotonin 1a and 2a receptors has been made. The competitive binding profiles of (±)-14 at these other CNS sites are summarized in Table 2, where the assay conditions are defined. The data reveal that compound (±)-14 does not have appreciable specific binding at other CNS binding sites that have been tested. Thus, compound (±)-14 is considered to have potent NET selectivity (Table 1, Example X) relative to the potencies at the other sites as defined per Table 2.

TABLE 2

| CNS Target Protein | $K_i$ of (±)-14 (nM) | Competition Radioligand | Nonspecific Binding (1 mM) | Assay Incubation Conditions | Assay Method Reference |
|---|---|---|---|---|---|
| SERT[a] | 1,798 | [$^3$H]Citalopram | Clomipramine | 25° C., 1 h | D'Amato 1987 |
| DAT[a] | 1,575 | [$^3$H]B-CFT | GBR-12,909 | 0° C., 2 h | Owens 1997 |
| β-Adrenergic[a] | 2.4 × 10$^5$ | [$^{125}$I]Iodopindalol | Alprenolol | 37° C., 1 h | Kalaria 1989 |
| 5-HT$_{1A}$[b] | NB[c] | [$^3$H]8-OH-DPAT | 5-HT | 30° C., 0.5 h | Russo 2005 |
| 5-HT$_{2A}$[b] | NB[c] | [$^3$H]Ketanserin | Mianserin | 30° C., 0.5 h | Russo 2005 |

[a]Partially purified rat protein.
[b]Partially purified human protein expressed in Chinese hamster ovary (CHO) cells.
[c]NB = no binding: no appreciable specific binding observed between concentrations 1 × 10$^{-5}$ to 1 × 10$^{-12}$ M.

EXAMPLE XII

Tracer Brain Imaging and Quantitative NET Detection in Rodent Subjects

As an example of the tracers of the invention, rodent (rat) quantitative in vivo PET imaging trials are presented employing the tracer (±)-[$^{18}$F]28 of Example VIII. The in vivo PET imaging was performed in parallel with magnetic resonance (MR) and computed axial tomography (CAT) imaging methods, in which the latter two imaging methods afforded anatomical tissue information for co-registration to the acquired tracer quantitative PET data. The co-registration of imaging data sets allows for the definitions of tissue regions of interest (ROIs) that possess various NET tissue densities (concentrations). Two rodent imaging trials (A-B) were performed employing two age-matched female Sprague-Dawley subjects. The age of the subjects were nearly identical to those described in the most recent rat (Sprague-Dawley, amongst others) stereotaxic brain atlas [Paxinos 2007] providing high confidence levels for identification and definition of explicit brain cerebral fine structures as regions of interest (ROIs) for quantitative analysis, and as a function of three-dimensional (3D) co-registration of cerebral soft tissue identification by MR analysis and landmark anatomical features from CAT data. Details of the two subject (A and B) imaging tracer trial are summarized in Table 3.

views were centered as bregma=origin of trial A. Consistent landmark structures were iteratively co-registered and template fit against the cranial structures of the trial A landmarks, and cross checked against cerebral soft tissues observed from the MR scan data. All PET scan data were decay time corrected, quantified with a phantom instrument calibration factor, and normalized by injected dose and dose specific activity (for example, divided by the specific activity in units mCi/nMol) to enable comparisons across subjects.

Each PET data set was iteratively co-registered to respective CT skull data and fine adjustments were made using the experiment A microPET data as a template. ROIs were drawn conservatively (well within the ROI volume size limits and locations) against their stereotaxic 3D locations [Paxinos 2007] and correlated with the MR tissue landmarks. The ROIs are defined in Table 4 as 3D coordinates x, y, z millimeters from bregma; LC as locus ceruleus, TH as thalamus, CE as cerebellum, FrCTX as frontal cortex, and OcCTX as occipital cortex. The analyzed ROI mean volume size (mm$^3$) and the mean number of voxels per ROI were calculated with AMIDE (Table 4). ROI PET scan statistics were exported to Excel and the graph of FIG. 1 was generated using GraphPad Prism software.

TABLE 3

| Trial | Rat Subject Age (days) | Rat Subject Weight (g) | Tracer Form | Tracer Specific Activity (mCi/μmol) | Tracer Dose (mCi) | Dose Volume (mL) | (±)-Nisoxetine Co-administration (2 mg/Kg dose) |
|---|---|---|---|---|---|---|---|
| A | 90 | 247 | (±)-[$^{18}$F]28 | 440 | 1.70 | 0.65 | None |
| B | 84 | 249 | (±)-[$^{18}$F]28 | 820 | 1.96 | 0.26 | 0.5 mg |

The PET data were acquired with a Siemens MicroPET II Focus 120 scanner (ca. 1.5 mm spatial resolution) [Tai 2004, Yang 2004]. Rodent subject tail vein tracer injection volumes were as described (Table 3) in saline followed by 0.3 mL saline flush. The co-administration injection of the NET inhibitor drug (±)-nisoxetine used 0.5 mg (±)-nisoxetine (2 mg/kg dose) in 0.1 mL saline followed by 0.2 mL saline into the subject's tail vein 15 minutes prior to tracer administration. Imaging was performed within a northermic (35° C.) multi-modal rodent imaging chamber under anesthesia (isoflurane 1.5-2.5%). The dynamic microPET data with tracer (±)-[$^{18}$F]28 were reconstructed as 37 frames (10 frames for 60 sec, 5 frames×120 sec, 8 frames×300 sec, 6 frames×600 sec, 8 frames×900 sec) over 4 h. Magnetic resonace (MR) data were acquired with a Bruker Biospin 7-Tesla magnet multi-slice 2D FLASH (T2*-weighted gradient recall echo, TR=1528.3 msec, TE=7 msec, 256×256×50 voxels, 16 μm$^3$ resolution). Computed axial tomography (CAT) data were acquired with a Siemens MicroCAT II scanner in standard rat mode (80 kVp, 225 mA; 400 ms exposure, 194 steps×194 degrees, 97 micron isotropic resolution).

MR, microCAT and microPET files were processed with AMIDE open source software [Loening 2003], version 0.9.0. MR and CT images were oriented as defined by Paxinos [2007]. Cranial landmarks of bregma and lambda were identified from the CT images. The X, Y, Z coordinates of imaging

TABLE 4

| ROIs | Average Size (mm$^3$) | Average Number Voxels | Distances from bregma (mm) | | |
|---|---|---|---|---|---|
| | | | x | y | z |
| LC | 0.65 | 6 | ±1.11 | −9.90 | 6.98 |
| TH | 15.7 | 63 | 0.00 | −2.52 | 6.19 |
| CE | 169.2 | 424 | 0.24 | −12.66 | 3.55 |
| FrCTX | 54.2 | 160 | 0.00 | 3.99 | 3.51 |
| OcCTX | 16.66 | 72 | 0.00 | −6.12 | 0.83 |

Known ROI NET tracer detection and binding distributions derived from autoradiographic studies carried out by others [Tejani-Butt 1992, Smith 2006] were used to compare relative cerebral ROI NET binding distributions from the rodent PET scan imaging studies. The relative comparisons of NET binding densities between the ROIs are particularly meaningful when extrapolated to the rodent PET scan data. The performance of tracer (±)-[$^{18}$F]28 alone (baseline scan, unblocked) and challenged (in the presence of (±)-nisoxetine, 2.0 mg/Kg; blocked) in key regions of interest over time is shown in graphically below in FIG. 1.

The tracer time-activity curves of FIG. 1 reveal the injected tracer penetrates brain, and at various times post injection discrete portions of the tracer dose (% ID/cc) tissue per ROI are observed. Tracer tissue activity pharmacokinetic curves are observed with tracer uptake, maximum and washout phases. The NET density rich locus coeruleus and thalamus are with the highest (±)-[$^{18}$F]28 tracer activities (2-6 min post injection) indicative of NET interactions. Cerebellum, and frontal cortex are with intermediate tracer activity within the same time frame. Lower NET interaction tracer activity was found in occipital cortices. The quantitative (±)-[$^{18}$F]28 tracer profiles have specific ROI NET tracer binding activities; for locus ceruleus, thalamus, cerebellum, frontal cortex and occipital cortex regions. Further, the (±)-[$^{18}$F]28 tracer NET detection distribution values generally agree with the relative NET distribution densities per ROI determined by autoradiography using the same species and another radiotracer agent [Tejani-Butt, 1993 & 1992]. Thus, NET is detected quantitatively in discrete cerebral ROIs with various known NET distributions across rat subject brain.

The FIG. 1 (±)-nisoxetine co-administration study (2 mg/Kg dose, blocking) reveals a significant reduction (2-5% ID/cc) for all ROI tracer (±)-[$^{18}$F]28 NET interaction activities. The co-administration of the known NET inhibitor (±)-nisoxetine affords significantly reduced (±)-[$^{18}$F]28 tracer interactions at the NET. These observations provide evidence that (±)-[$^{18}$F]28 interacting with NET in a specific way.

EXAMPLE XIII

Tracer Brain Imaging and Quantitative NET Detection in Primate Subject

Another example of the radiotracers of the invention includes the in vivo performance for the quantitative detection of NET and NET tissue distribution profiles in live primate brain. For example, imaging tracer (S)-[$^{18}$F]28 of Example IX has been evaluated in male Rhesus monkey (*Macaca mulatta*, male, 8.53 kg, 7 years old) with quantitative positron emission tomography (PET) and magnetic resonance (MR) imaging scans across brain. The PET imaging scans allowed the determinations of quantitative detection of NET distributions within cerebral tissue regions of interest (ROIs). The MR scans allowed the determinations of soft tissue ROIs that were co-registered with the three-dimensional (3D) brain tissue NET tracer activities determined with the dynamic PET imaging. Typical brain scan methods are as follows.

The imaging subject (nor-thermic, 35° C.) was placed under anesthesia, initially with saphenous catheter administration of 0.9 mL of 100 mg/mL ketamine, 0.9 mL of 0.4 mg/mL atropine, and followed by 1-1.5% isoflurane ventilation. MR scan data were acquired with a GE Signa LX (Milwaukee, Wis.) 1.5-Tesla magnet and quadrature head coil. A 3-axis MR scout scan was initially run to determine localization coordinates. The subject was positioned within the MR scanner head first in sternal recumbancy. MR cerebral scan images were acquired using a T1-weighted 3D SPGR sequence with the following parameters: TR=22 msec, TE=7.9 msec, FA=30 degrees, RBw=15.63 kHz, 4 averages, 256×256 matrix, 84×1 mm slices, 16 cm field of view, and 625 µm in-plane resolution). A fiducial marker (vitamin E filled) on the left side of the subject's head was used to mark the MR scan head orientation for subsequent MR-PET scan co-registrations.

The PET scan data were acquired with a Siemens Micro-PET P4 Focus scanner that is characterized with ca. 1.8 mm$^3$ spatial resolution at center of the field of view [Tai et al. 2001]. Administration of the tracer (S)-[$^{18}$F]28 was by bolus injection via the saphenous catheter. The tracer dose was a 2 mL saline injection volume containing 8.57 mCi (37.75 nmol) of tracer (S)-[$^{18}$F]28 with a determined specific activity of 227 mCi/µmol. Dynamic PET scan data were acquired over a 1.5 h period post injection of tracer. The dynamic PET scan data were reconstructed with a maximum a priori (MAP) protocol with output as Concorde/microPET image files. The scan data reconstruction parameters were as follows: 0.8 mm in-plane resolution, smoothing parameter of 0.1, MAPTR attenuation/scatter correction, and as either a single frame (1 frame for 5400 s) or 27 frames (10 frames for 60 s, 5 frames for 120 s, 8 frames for 300 s, and 3 frames for 600 s) for a total of 90 minutes.

The MR and microPET files were processed and co-registered with AMIDE open source software [Loening 2003]. The co-registration of MR and PET data sets were as follows. The centers of the cerebral tissues of the anterior and posterior commissures were identified and used as key 3D brain tissue landmarks. MR images were oriented to place the vitamin E fiducial mark consistent with the axes in AMIDE and as per the *Rhesus Monkey Brain in Stereotaxic Coordinates* atlas [Paxinos 2000], and also the BrainInfo *Macaca fascicularis* line drawings/sectional slices of the online atlas http://braininfo.rprc.washinFton.edu and the BrainMaps.org *Mucaca mulatta* sectional slice online atlas http://brainmaps.org. Using these atlases, the respective views and the tissue landmarks therein, the subject brain tissues were oriented in a sagittal perspective facing left, anterior and posterior commissure marks in the same horizontal plane, and the coronal and transverse views symmetrical about the brain medial line.

The x, y, and z 3D coordinate origin was defined for the cerebral views as the center of the anterior commissure; as per the online atlases of the http://braininfo.rprc.washington.edu and http://brainmaps.org. The single frame reconstructed PET data was iteratively co-registered to the MR data. For example, MR soft tissue landmarks were correlated with the PET scan landmarks (including: eyes, jaw-line, connective tissue, amongst others) affording discrete co-registered planes of recognized views. After co-registration, a transformation matrix that defined a center and rotational coordinates from the single frame PET data were made. The transformation matrix was applied to the dynamic (27 frame) PET data sets to obtain an identical co-registration as per the single frame data.

The cerebral ROIs were drawn conservatively against their stereotaxic 3D locations ([Paxinos 2007], and also http://braininfo.rprc.washington.edu and http://brainmaps.org). The cerebral locations are defined in Table 5 (ROI x, y, z millimeters from anterior commissure). The ROIs are defined as BSTM as brain stem (including locus coeruleus, lateral tegemental nuclei, dorsal raphe nuclei, and pontine nuclei), CE as cerebellum, TH as thalamus (primarily, dorsolateral thalamic nuclei), and FrCTX as frontal cortices (including, somatosens and motor cortices). The analyzed ROI volume size (mm$^3$) and the number of voxels per ROI were calculated with AMIDE as per Table 5.

All dynamic PET data were decay and time corrected. The corrected scan data were subsequently normalized by the following protocol: 1) multiplication by the instrument calibration factor determined by phantom PET scan, 2) division by tracer injected dose (mCi), and 3) division by tracer specific activity. The graphical image analyses employed an NIH rainbow table with max-min global thresholds set to 25 to 2 percent of % ID/cc. PET data reconstructions afforded 1.2 mm$^3$ voxel (pixel volumes) size for the frame data sets. ROI PET scan statistics were exported to Excel and the graph of FIG. 2 was generated using GraphPad Prism software.

TABLE 5

| ROI | ROI Values | | Distances from Anterior Commissure (mm) | | |
| --- | --- | --- | --- | --- | --- |
| | Size (mm³) | Voxel Numbers | x | y | z |
| BSTM | 221 | 283 | 0.00 | 17.28 | −8.53 |
| CE | 3888 | 3866 | 0.00 | 31.38 | −9.64 |
| TH | 133 | 190 | ±6.84 | 10.67 | 2.02 |
| FrCTX | 2599 | 2888 | 0.00 | 1.33 | 19.12 |

The tracer time-activity curves of FIG. 2 reveal the injected tracer penetrates brain, and at various times post injection discrete portions of the tracer dose (% ID/cc) tissue per ROI are observed. Tracer tissue activity pharmacokinetic curves are observed with tracer uptake, maximum and washout phases over the course of 1.5 h. Tracer tissue maxima occurred at between 10-20 min post injection. The NET density rich thalamus, frontal cortex and cerebellum regions are with the high (S)-[$^{18}$F]28 tracer activities indicative of NET interactions. Tracer activity in the brainstem, which includes a number of brain structures, has higher NET detection tracer activities at later times. The quantitative (S)-[$^{18}$F]28 tracer profiles have specific ROI NET tracer binding activities; for locus ceruleus, thalamus, cerebellum and frontal cortex regions. Further, the (S)-[$^{18}$F]28 tracer NET detection distribution values generally agree with the relative NET distribution densities per ROI determined by autoradiography using the same subject species and another radiotracer agent [Smith 2006]. Thus, with the tracers of the invention NET is detected quantitatively in discrete cerebral ROIs with various known NET density distributions across primate brain. The tracers of the invention are observed with unique pharmacokinetic profiles for the quantitative detection of NET and NET distributions in brain regions of primate subjects, relative to other NET PET imaging tracers [Logan 2007 & 2005, Ding 2006 & 2005, Seneca 2006, Schou 2004 & 2003].

It is understood that the foregoing examples are merely illustrative of the present invention. Certain modifications of the articles and/or methods may be made and still achieve the objectives of the invention. Such modifications are contemplated as within the scope of the claimed invention.

REFERENCES

Bedurftig S, Wunsch B (2004) Chiral, nonracemic (piperazin-2-yl)methanol derivatives with [sigma-receptor affinity. Bioorg Med Chem 12:3299-3311.

Bedurftig S, Wunsch B (2006) Synthesis and receptor binding studies of 3-substituted piperazine derivatives. Eur J Med Chem 41:387-396.

Bonisch H, Bruss M (2006) The norepinephrine transporter in physiology and disease. Handbook of Experimental Pharmacology 175:485-525.

Bymaster F P, Katner J S, Nelson D L, Henrick-Luecke S K, Threlkeld P G, Heiligenstein J H, Morin S M, Gehlert D R, Perry K W (2002) Atomoxetine increases extracellular levels of norepinephrine and dopamine in prefrontal cortex of rat: a potential mechanism for efficacy in attention deficit/hyperactivity disorder. Neuropsychopharmacology 27:699-711.

Cannistraro P A, Rauch S L (2003) Neural circuitry of anxiety: evidence from structural and functional neuroimaging studies. Psychopharmacol Bull 37:8-25.

Cheng Y C, Prusoff W H (1973) Relationship between the inhibition constant ($K_i$) and concentration of inhibitor which causes 50 percent inhibition ($IC_{50}$) of enzyme reaction Biochem Pharmacol 22:3099-3108.

D'Amato R J, Largent B L, Snowman A M, Snyder S H (1987) Selective labeling of serotonin uptake sites in rat brain by [$^3$H]citalopram contrasted to labeling of multiple sites by [$^3$H]imipramine. J Pharmacol Exp Ther 242:364-371.

Ding Y-S, Lin K-S, Logan J (2005) PET imaging of norepinephrine transporters. Current Pharmaceutical Design 12:3831-3845.

Ding Y—S, Lin K-S, Logan J, Bienveniste H, Carter P (2006) Comparative evaluation of positron emission tomography radiotracers for imaging the norepinephrine tranporter: (S,S) and (R,R) enantiomers of reboxetine analogs ([$^{11}$C]methylreboxetine, 3-Cl-[$^{11}$C]methylreboxetine and [$^{18}$F]fluororeboxetine), (R)-[$^{11}$C]nisoxetine, [$^{11}$C]oxaprotiline, and [$^{11}$C]lortalamine. J Neurochem 94:337-351.

Gerdes J M, DeFina S C, Wilson P A, Taylor SE (2000) Serotonin transporter inhibitors: synthesis and binding potency of 2'-methyl- and 3'-methyl-6-nitroquipazine. Bioorg Med Chem Lett 10:2643-2646.

Gilman H, Crounse N N, Massie S P, Benkeser R A J, Spatz S M, (1945) Rearrangement in the reaction of alpha-halogenonaphthalenes with lithium diethylamide. J Am Chem Soc 67:2106-2108.

Hajos M, Fleishaker J C, Filipiak-Reisner J K, Brown M T, Wong E H F (2004). The selective norepinephrine reuptake inhibitor antidepressant reboxetine: pharmacological and clinical profile. CNS Drug Reviews 10:23-44.

Hoye T R, Renner M K (1996) MTPA (Mosher) amides of cyclic secondary amines: conformational aspects and a useful method for assignment of amine configuration. J Org Chem 61:2056-2064.

Kalaria R N, Andom A C, Tabaton M, Whitehouse P J, Harik S I, Unnerstall J R. (1989) Adrenergic receptors in aging and Alzheimer's Disease: increased β2-receptors in prefrontal cortex and hippocampus. J Neurochem 53:1772-1781.

Klimek V, Stockmeir C, Overholser J, Meltzer H Y, Kalka S, Dilley G, Ordway G A (1997) Reduced levels of norepinephrine transporters in the locus coeruleus in major depression. J Neurosci 17:8451-8458.

Loening A M, Gambhir S S (2003) AMIDE: a free software tool for multimodality medical image analysis. Molecular Imaging 2:131-137.

Logan J, Wang G-J, Telang F, Fowler J S, Axeloff D, Zabrowski J, Jane M, Hubbard B, King P, Carter P, Shea C, Xu Y, Muench L, Schlyer D, Learned-Coughlin S, Cosson V, Volkow N D, Ding Y-S (2007) Imaging the norepinephrine transporter in humans with (S,S)-[$^{11}$C]O-methyl reboxetine and PET: problems and progress. Nuc Med Biol 34:667-679.

Logan J, Ding Y-S, Lin K-S, Pareto D, Fowler J, Biegon A (2005) Modeling and analysis of PET studies with norepinephrine transporter ligands: the search for a reference region. Nuc Medicine and Biology 32:531-542.

Madela P, Ordway G A (2006) The norepinephrine transporter and its regulation. J Neurochem 97:310-333.

Millan M J (2006) Multi-target strategies for improved treatment of depressive states: conceptual foundations and neuronal substrates, drug discovery and therapeutic application. Pharmacol and Therapeutics 110: 135-370.

Millan M J Lejeune F, Goibert A (2000) Reciprocal autoreceptor and heteroreceptor control of serotonergic, dopaminergeric, and adrenergic transmission in the frontal cortex:

a review, and relevance to the actions of antidepressant agents. J Pharmacol 14:114-138.

Naylor A, Judd D B, Lloyd J E, Scopes D I C, Hayes A G, Birch P J (1993) A potent new class of k-receptor agonists: 4-substituted 1-(arylacetyl)-2-[(dialkylamino)methyl]-piperazines. J Med Chem 36:2075-2083.

Ordway G A (1997) Pathophysiology of the locus coeruleus in suicide. Ann NY Acad Sci 836:233-252.

Owens M J, Morgan W N, Plott M S, Nemeroff C B (1997) Neurotransmitter receptor and transporter binding profile of antidepressants and their metabolites. J Pharmacol Exp Ther 283:1305-22.

Paxinos G, Watson C (2007) The Rat Brain in Stereotaxic Coordinates, 6$^{th}$ edition. Elsevier, Burlington, Mass.

Paxinos G, Huang V F, Toga A W (2000) The Rhesus Monkey Brain in Stereotaxic Coordinates. Academic Press: Burlington, Mass.

Raisman R, Sette M, Pimoule C, Briley M, Langer S Z (1982) High-affinity [$^3$H]desipramine binding in the peripheral and central nervous system: a specific site associated with neuronal uptake of noradrenaline. Eur. J. Pharmacol 78:345-351.

Robinson R A (1947) 1-Dialkylaminoalkylminoisoquinolines. J Am Chem Soc 69:1939-1942.

Rommelfanger K S, Weinshenker D (2007) Norepinephrine: the redheaded stepchild of Parkinson's disease. Biochem Pharmacol 74:177-190.

Rondu F, Le Bihan G, Wang X, Lamouri A, Touboul E, Dive G, Bellahsene T, Pfeiffer B, Renard P, Guardiola-Lemaitire B, Manachez D, Penicaud L, Ktorza A, Godffroid J-J (1997) Design and synthesis of imidaoline derivatives active on glucose homeostasis in a rat model of type II diabetes. 1. Synthesis and biological activities of N-benzylN'-(arlalkyl)-2-(4',5'-dihydro-1'HH-imidazol-2'-yl) piperazines. J Med Chem 40:3793-3803.

Russo E B, Burnett A, Hall B, Parker K K (2005) Agonist properties of cannabidiol at 5-HT1a receptors. Neurochem Res 30:1037-1043.

Schou M, Halldin C, Sovago J, Pike V W, Hall H, Gulyas B, Mozley P D, Dobson D, Shcukin E, Innis R B, Farde L (2004) PET evaluation of novel radiofluorinated reboxetine analogs as norepinepthrine transporter probes in the monkey brain. Synapse 53:57-67.

Schou M, Halldin C, Sovago J, Pike V W, Gulyas B, Mozley P D, Johnson D P, Hall H, Innis R B, Farde L (2003) Specific in vivo binding to the norepinephrine transporter demonstrated with PET radioligand (S,S)-[$^{11}$C]MeNER. Nuc Med Biol 30:707-714.

Seneca N, Gulyas B, Varrone A, Schou M, Airaksinen A, Tauscher J, Vandehende F, Kielbasa W, Farde L, Innis R B, Halldin C (2006) Atomoxetine occupies the norepinephrine transporter in a dose-dependent fashion: a PET study in nonhuman primate brain using (S,S)-[$^{18}$F]FMeNER-D$_2$. Psychopharmacol 188:119-127.

Smith M B, March J (2001) March's Advanced Organic Chemistry: Reactions, Mechanism and Structure; 5$^{th}$ Edition. Wiley-Interscience: New York.

Smith H R, Beveridge T J R, Porrino L J (2006) Distribution of norepinephrine transporters in the non-human brain. Neurosci 138:703-714.

Stone E A, Quaterman D (2005) The brain epinephrine-alpha1-adrenoreceptor system in behavioural activation and depression. Current Psychiatr Rev 1:33-43.

Tai Y C, Ruangma A, Rowland D, Siegel S, Newport D F, Chow P L, Laforest R (2005) Performance evaluation fo the microPET focus: a third generation microPET scanner dedicated to animal imaging. J Nuc Med 46:455-463.

Tai C, Chatziioannou A, Siegel S, Young J, Newport D, Goble R N, Nutt R E, Chemy S R (2001) Performance evaluation of the microPET P4: a PET system dedicated to animal imaging. Phys Med Biol 46:1845-62.

Tamagnan G D, Brenner E, Alagille D, Staley J K, Haile C, Koren A Early M, Baldwin R M, Tarazi F I, Baldessarini R J, Jarkas N, Goodman M M, Seibyl J P (2007) Development of SPECT imaging agents for the norepinephrine transporters: [$^{123}$I]INER. Bioorg Med Chem Lett 17:533-537.

Tejani-Butt S M, Yang J, Zaffar H (1993) Norepineprhine transporter sites are decreased in the locu coeruleus in Alzheimer's disease. Brain Res 631:147-150.

Tejani-Butt S M (1992) Effect of age on [$^3$H]nisoxetine binding to uptake sites for norepinephrine in the locus coeruleus of humans. Brain Res 583:312-315.

Tejani-Butt S M (1992) [$^3$H]Nisoxetine: a radioligand for qunatitation of norepinephrine uptake sites by autoradiography or by homogenate binding. J Pharmacol Exp Therapeutics 260:426-436.

Vieweg W V, Julies D A, Fernandez A, Beatty-Brooks M, Hettema J H, Pandurangi A K (2006) Posttraumatic stress disorder: clinical features, pathophysiology, and treatment. Am J Med 119:383-390.

Yang Y, Tai Y C, Siegel S, Newport D F, Bai B, Li Q, Leahy R M, Chemy S R (2004) Phys Med Biol 49:2527-2545.

Zhou J (2004) Norepinephrine transporter inhibitors and their therapeutic potential. Drugs Future 29:1235-1244.

We claim:

1. A compound having the following structure:

[Chemical structure: an isoquinoline ring system with substituents $R_3$, $R_4$, $R_5$, $R_6$, $R_7$ on the aromatic ring (positions 3, 4, 5, 6, 7 respectively), N at position 1 connected to a piperidine ring bearing $R_2$ at position 2' (marked with *) and $R_1$ on the nitrogen at position 4']

wherein, * independently denotes an R or S configuration or a racemic mixture; and wherein $R_1$ is selected from the group consisting of H, methyl, alkyl, and halo-alkyl; and wherein $R_2$ is selected from the group consisting of straight chain alkyl, branched alkyl, O-alkyl, S-alkyl, aryl-alkyl-, halo-substituted-alkyl-, halo-substituted-alkenyl-, substituted-alkenyl-, alkyl-oxy-alkyl ether-, halo-substituted-alkyl-oxy-alkyl ether-, aryl-oxy-alkyl ether-, O-aryl, S-aryl, amino, amino-alkyl, and amino-aryl; and wherein $R_3$ is selected from the group consisting of H, halogen, straight chain alkyl, branched alkyl, O-alkyl, S-alkyl, aryl-alkyl-, halo-substituted-alkyl, halo-substituted-alkenyl-, substituted-alkenyl-, alkyl-oxy-alkyl ether-, halo-substituted-alkyl-oxy-alkyl ether-, aryl-oxy-alkyl ether-, O-aryl, S-aryl, amino, amino-alkyl, and amino-aryl; and wherein $R_4$, $R_5$, $R_6$, and $R_7$ are independently selected from the group consisting of H, halogen, straight chain alkyl, branched alkyl, O-alkyl, halo-substituted-alkyl-, halo-substituted-alkenyl-, substituted-alkenyl-, carboxyl acid, or carboxylic ester, nitro, amino, and substituted-amino.

2. A pharmaceutical composition comprising a compound having the following structure:

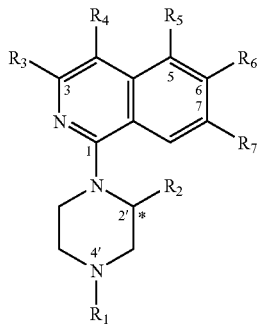

wherein, * independently denotes an R or S configuration or a racemic mixture; and wherein $R_1$ is selected from the group consisting of H, methyl, alkyl, and halo-alkyl; and wherein $R_2$ is selected from the group consisting of straight chain alkyl, branched alkyl, O-alkyl, S-alkyl, aryl-alkyl-, halo-substituted-alkyl-, halo-substituted-alkenyl-, substituted-alkenyl-, alkyl-oxy-alkyl ether-, halo-substituted-alkyl-oxy-alkyl ether-, aryl-oxy-alkyl ether-, O-aryl, S-aryl, amino, amino-alkyl, and amino-aryl; and wherein $R_3$ is selected from the group consisting of H, halogen, straight chain alkyl, branched alkyl, O-alkyl, S-alkyl, aryl-alkyl-, halo-substituted-alkyl, halo-substituted-alkenyl-, substituted-alkenyl-, alkyl-oxy-alkyl ether-, halo-substituted-alkyl-oxy-alkyl ether-, aryl-oxy-alkyl ether-, O-aryl, S-aryl, amino, amino-alkyl, and amino-aryl; and wherein $R_4$, $R_5$, $R_6$, and $R_7$ are independently selected from the group consisting of H, halogen, straight chain alkyl, branched alkyl, O-alkyl, halo-substituted-alkyl-, halo-substituted-alkenyl-, substituted-alkenyl-, carboxyl acid, or carboxylic ester, nitro, amino, and substituted-amino; and at least one pharmaceutically acceptable carrier.

3. A method of treating depression comprising the steps of: administering to a subject in need thereof a compound having the following structure:

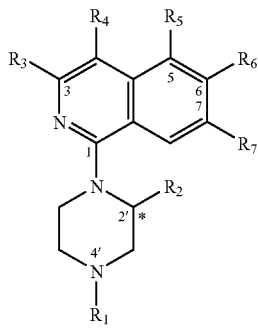

wherein, * independently denotes an R or S configuration or a racemic mixture; and wherein $R_1$ is selected from the group consisting of H, methyl, alkyl, and halo-alkyl; and wherein $R_2$ is selected from the group consisting of straight chain alkyl, branched alkyl, O-alkyl, S-alkyl, aryl-alkyl-, halo-substituted-alkyl-, halo-substituted-alkenyl-, substituted-alkenyl-, alkyl-oxy-alkyl ether-, halo-substituted-alkyl-oxy-alkyl ether-, aryl-oxy-alkyl ether-, O-aryl, S-aryl, amino, amino-alkyl, and amino-aryl; and wherein $R_3$ is selected from the group consisting of H, halogen, straight chain alkyl, branched alkyl, O-alkyl, S-alkyl, aryl-alkyl-, halo-substituted-alkyl, halo-substituted-alkenyl-, substituted-alkenyl-, alkyl-oxy-alkyl ether-, halo-substituted-alkyl-oxy-alkyl ether-, aryl-oxy-alkyl ether-, O-aryl, S-aryl, amino, amino-alkyl, and amino-aryl; and wherein $R_4$, $R_5$, $R_6$, and $R_7$ are independently selected from the group consisting of H, halogen, straight chain alkyl, branched alkyl, O-alkyl, halo-substituted-alkyl-, halo-substituted-alkenyl-, substituted-alkenyl-, carboxyl acid, or carboxylic ester, nitro, amino, and substituted-amino.

4. A radiotracer having the following structure:

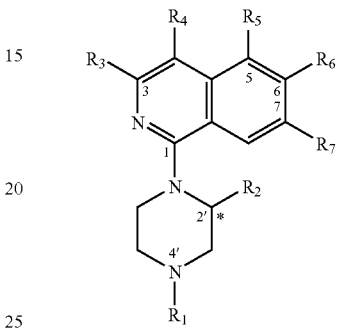

wherein, * independently denotes an R or S configuration or a racemic mixture; and wherein $R_1$ is selected from the group consisting of H, methyl, alkyl, halo-alkyl, and $^3H$, $^{18}F$, and $^{11}C$; and wherein $R_2$ is selected from the group consisting of straight chain alkyl, branched alkyl, O-alkyl, S-alkyl, aryl-alkyl-, halo-substituted-alkyl-, halo-substituted-alkenyl-, substituted-alkenyl-, alkyl-oxy-alkyl ether-, halo-substituted-alkyl-oxy-alkyl ether-, aryl-oxy-alkyl ether-, O-aryl, S-aryl, amino, amino-alkyl, amino-aryl, and $^3H$, $^{18}F$, $^{75}Br$, $^{76}Br$, $^{123}I$, $^{124}I$, $^{125}I$, $^{131}I$, and $^{11}C$; and wherein $R_3$ is selected from the group consisting of H, halogen, straight chain alkyl, branched alkyl, O-alkyl, S-alkyl, aryl-alkyl-, halo-substituted-alkyl-, halo-substituted-alkenyl-, substituted-alkenyl-, alkyl-oxy-alkyl ether-, halo-substituted-alkyl-oxy-alkyl ether-, aryl-oxy-alkyl ether-, O-aryl, S-aryl, amino, amino-alkyl, amino-aryl, and $^3H$, $^{18}F$, $^{75}Br$, $^{76}Br$, $^{123}I$, $^{124}I$, $^{125}I$, $^{131}I$, and $^{11}C$; and wherein $R_4$, $R_5$, $R_6$, and $R_7$ are independently selected from the group consisting of H, halogen, straight chain alkyl, branched alkyl, O-alkyl, halo-substituted-alkyl-, halo-substituted-alkenyl-, substituted-alkenyl-, carboxyl acid, carboxylic ester, and $^3H$, $^{18}F$, $^{75}Br$, $^{76}Br$, $^{123}I$, $^{124}I$, $^{125}I$, $^{131}I$, and $^{11}C$.

5. A pharmaceutical composition comprising a radiotracer having the following structure:

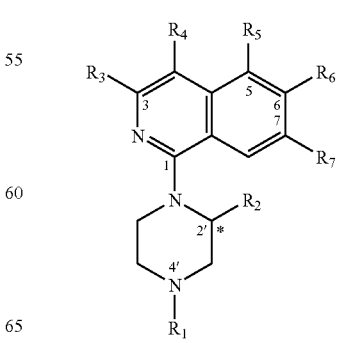

wherein, * independently denotes an R or S configuration or a racemic mixture; and wherein $R_1$ is selected from the group consisting of H, methyl, alkyl, halo-alkyl, and $^3$H, $^{18}$F, and $^{11}$C; and wherein $R_2$ selected from the group consisting of alkyl (straight chain or branched), O-alkyl, S-alkyl, aryl-alkyl-, halo-substituted-alkyl-, halo-substituted-alkenyl-, substituted-alkenyl-, alkyl-oxy-alkyl ether-, halo-substituted-alkyl-oxy-alkyl ether-, aryl-oxy-alkyl ether-, O-aryl, S-aryl, amino, amino-alkyl, amino-aryl, $^3$H, $^{18}$F, $^{75}$Br, $^{76}$Br, $^{123}$I, $^{124}$I, $^{125}$I, $^{131}$I, and $^{11}$C; and wherein $R_3$ is selected from the group consisting of H, halogen, straight chain alkyl, branched alkyl, O-alkyl, S-alkyl, aryl-alkyl-, halo-substituted-alkyl-, halo-substituted-alkenyl-, substituted-alkenyl-, alkyl-oxy-alkyl ether-, halo-substituted-alkyl-oxy-alkyl ether-, aryl-oxy-alkyl ether-, O-aryl, S-aryl, amino, amino-alkyl, amino-aryl, and $^3$H, $^{18}$F, $^{75}$Br, $^{76}$Br, $^{123}$I, $^{124}$I, $^{125}$I, $^{131}$I, and $^{11}$C; and wherein $R_4$, $R_5$, $R_6$, and $R_7$ are independently selected from the group consisting of H, halogen, straight chain alkyl, branched alkyl, O-alkyl, halo-substituted-alkyl-, halo-substituted-alkenyl-, substituted-alkenyl-, carboxyl acid, carboxylic ester, and $^3$H, $^{18}$F, $^{75}$Br, $^{76}$Br, $^{123}$I, $^{124}$I, $^{125}$I, $^{131}$I, and $^{11}$C; and at least one pharmaceutically acceptable carrier.

6. A method for in vivo imaging comprising the steps of administering to a subject a radiotracer having the following structure:

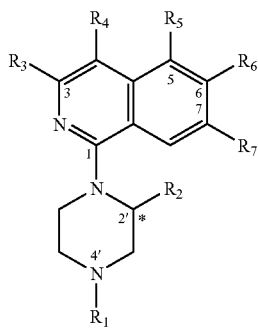

wherein, * independently denotes an R or S configuration or a racemic mixture; and wherein $R_1$ is selected from the group consisting of H, methyl, alkyl, halo-alkyl, and $^3$H, $^{18}$F, and $^{11}$C; and wherein $R_2$ is selected from the group consisting of straight chain alkyl, branched alkyl, O-alkyl, S-alkyl, aryl-alkyl-, halo-substituted-alkyl-, halo-substituted-alkenyl-, substituted-alkenyl-, alkyl-oxy-alkyl ether-, halo-substituted-alkyl-oxy-alkyl ether-, aryl-oxy-alkyl ether-, O-aryl, S-aryl, amino, amino-alkyl, amino-aryl, and $^3$H, $^{18}$F, $^{75}$Br, $^{76}$Br, $^{123}$I, $^{124}$I, $^{125}$I, $^{131}$I, and $^{11}$C; and wherein $R_3$ is selected from the group consisting of H, halogen, straight chain alkyl, branched alkyl, O-alkyl, S-alkyl, aryl-alkyl-, halo-substituted-alkyl-, halo-substituted-alkenyl-, substituted-alkenyl-, alkyl-oxy-alkyl ether-, halo-substituted-alkyl-oxy-alkyl ether-, aryl-oxy-alkyl ether-, O-aryl, S-aryl, amino, amino-alkyl, amino-aryl, and $^3$H, $^{18}$F, $^{75}$Br, $^{76}$Br, $^{123}$I, $^{124}$I, $^{125}$I, $^{131}$I, and $^{11}$C; and wherein $R_4$, $R_5$, $R_6$, and $R_7$ are independently selected from the group consisting of H, halogen, straight chain alkyl, branched alkyl, O-alkyl, halo-substituted-alkyl-, halo-substituted-alkenyl-, substituted-alkenyl-, carboxyl acid, carboxylic ester, and $^3$H, $^{18}$F, $^{75}$Br, $^{76}$Br, $^{123}$I, $^{124}$I, $^{125}$I, $^{131}$I, and $^{11}$C; and detecting the radiotracer wherein the radiotracer is associated with the norepinephrine transporter protein.

7. The method of claim 6, further comprising the steps of imaging said subject to detect the distribution of norepinephrine transporter protein.

8. The method of claim 6, further comprising the steps of imaging said subject and analyzing the imaging data.

9. The method of claim 6, wherein said radiotracer is detected by imaging said subject, said method further comprising the steps of administering to said subject a therapeutic agent; administering to said subject said radiotracer; imaging said subject; and comparing a level of association of said tracer with the norepinephrine transporter protein in said subject before and after administering the therapeutic agent.

10. The method of claim 7, wherein imaging said subject is performed by an imaging modality selected from the group consisting of positron emission tomography, single photon emission computed tomography and combinations thereof.

11. A method for tissue imaging comprising the steps of contacting a tissue that contains norepinephrine transporter protein with a radiotracer having the following structure:

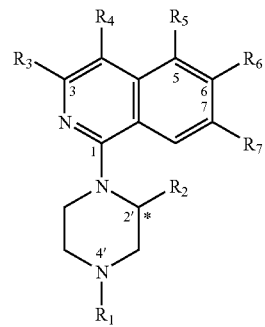

wherein, * independently denotes an R or S configuration or a racemic mixture; and wherein $R_1$ is selected from the group consisting of H, methyl, alkyl, halo-alkyl, and $^3$H, $^{18}$F, and $^{11}$C; and wherein $R_2$ is selected from the group consisting of straight chain alkyl, branched alkyl, O-alkyl, S-alkyl, aryl-alkyl-, halo-substituted-alkyl-, halo-substituted-alkenyl-, substituted-alkenyl-, alkyl-oxy-alkyl ether-, halo-substituted-alkyl-oxy-alkyl ether-, aryl-oxy-alkyl ether-, O-aryl, S-aryl, amino, amino-alkyl, amino-aryl, and $^3$H, $^{18}$F, $^{75}$Br, $^{76}$Br, $^{123}$I, $^{124}$I, $^{125}$I, $^{131}$I, and $^{11}$C; and wherein $R_3$ is selected from the group consisting of H, halogen, straight chain alkyl, branched alkyl, O-alkyl, S-alkyl, aryl-alkyl-, halo-substituted-alkyl-, halo-substituted-alkenyl-, substituted-alkenyl-, alkyl-oxy-alkyl ether-, halo-substituted-alkyl-oxy-alkyl ether-, aryl-oxy-alkyl ether-, O-aryl, S-aryl, amino, amino-alkyl, amino-aryl, and $^3$H, $^{18}$F, $^{75}$Br, $^{76}$Br, $^{123}$I, $^{124}$I, $^{125}$I, $^{131}$I, and $^{11}$C; and wherein $R_4$, $R_5$, $R_6$, and $R_7$ are independently selected from the group consisting of H, halogen, straight chain alkyl, branched alkyl, O-alkyl, halo-substituted-alkyl-, halo-substituted-alkenyl-, substituted-alkenyl-, carboxyl acid, carboxylic ester, and $^3$H, $^{18}$F, $^{75}$Br, $^{76}$Br, $^{123}$I, $^{124}$I, $^{125}$I, $^{131}$I, and $^{11}$C; and detecting the radiotracer.

12. A method of claim 11, wherein said radiotracer detected in vitro.

13. A method of claim 11, wherein said radiotracer detected ex vivo.

* * * * *